(12) United States Patent
Buettelmann et al.

(10) Patent No.: US 8,293,916 B2
(45) Date of Patent: *Oct. 23, 2012

(54) DIAZOLE DERIVATIVES

(75) Inventors: Bernd Buettelmann, Schopfheim (DE); Simona Maria Ceccarelli, Basel (CH); Georg Jaeschke, Basel (CH); Sabine Kolczewski, Rheinfelden (DE); Richard Hugh Philip Porter, Reinach (CH); Paul Spurr, Riehen (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 144 days.

This patent is subject to a terminal disclaimer.

(21) Appl. No.: 12/613,089

(22) Filed: Nov. 5, 2009

(65) Prior Publication Data

US 2010/0048569 A1   Feb. 25, 2010

Related U.S. Application Data

(63) Continuation of application No. 11/141,547, filed on May 31, 2005, now abandoned.

(30) Foreign Application Priority Data

Jun. 1, 2004  (WO) ................. PCT/EP2004/005881
Sep. 7, 2004  (EP) .................................... 04021216

(51) Int. Cl.
*A61K 31/4439* (2006.01)
*C07D 401/04* (2006.01)
*C07D 401/06* (2006.01)
*C07D 401/14* (2006.01)

(52) U.S. Cl. .................. 546/272.7; 546/274.1; 544/238; 544/322; 544/405; 514/341; 514/252.03; 514/255.05; 514/275

(58) Field of Classification Search .................. 544/238, 544/322, 405; 546/272.7, 274.1; 514/252.03, 514/255.05, 275, 341
See application file for complete search history.

(56) References Cited

U.S. PATENT DOCUMENTS

| | | |
|---|---|---|
| 3,045,022 A | 7/1962 | McGill |
| 3,303,199 A | 2/1967 | Doebel et al. |
| 3,341,548 A | 9/1967 | Hoffer |
| 4,352,818 A | 10/1982 | Hunkeler et al. |
| 4,508,560 A | 4/1985 | Brunner et al. |
| 4,711,962 A | 12/1987 | Leone-Bay |
| 6,596,731 B2 | 7/2003 | Mutel et al. |
| 6,831,175 B2 | 12/2004 | Li et al. |
| 6,872,690 B2 | 3/2005 | Maier |
| 7,151,098 B2 | 12/2006 | Adam et al. |
| 7,253,190 B2 | 8/2007 | Cosford et al. |
| 7,300,939 B2 | 11/2007 | Kuehnert et al. |
| 7,531,529 B2 | 5/2009 | Buettelmann et al. |
| 2002/0081655 A1 | 6/2002 | Savitzky et al. |
| 2004/0248888 A1 | 12/2004 | Buettelmann et al. |
| 2004/0259917 A1 | 12/2004 | Cosford et al. |

FOREIGN PATENT DOCUMENTS

| | | |
|---|---|---|
| DE | 2035905 | 2/1972 |
| EP | 059 390 | 9/1982 |
| EP | 1349839 | 10/2003 |
| EP | 1606277 | 12/2005 |
| EP | 1644351 | 4/2006 |
| EP | 1831193 | 9/2007 |
| WO | WO 91/00277 | 1/1991 |
| WO | WO 99/02497 | 1/1999 |
| WO | WO 99/08678 | 2/1999 |
| WO | WO 01/16121 | 3/2001 |
| WO | WO 02/08205 A1 | 1/2002 |
| WO | WO 02/46166 | 6/2002 |
| WO | WO 2004/038374 | 5/2004 |
| WO | 2004/067002 | 8/2004 |
| WO | WO 2004/080998 | 9/2004 |
| WO | WO 2004/108701 | 12/2004 |
| WO | WO 2005/003117 | 1/2005 |
| WO | WO 2005/023795 | 3/2005 |

OTHER PUBLICATIONS

Will, P.J.M., Trends in Pharmacological Sciences, 22:7, 331-337 (2001).
Buchwald et al, Tetrahedron Letters, 40:2657-2660 (1999).
Sonogashira et al, Synthesis, (1977) 777-778.
Sakamoto et al., Chem. Pharm. Bull., vol. 35(2) pp. 823-828 (1987).
Miller, et al., Chem. Mater., vol. 6(7) pp. 1023-1032 (1994).
Rapoport et al., Environ. Health Perspect. vol. 67, pp. 41-45 (1986).
Bond et al., Synth. Commun., vol. 19, pp. 2551-2566 (1989).
Sintas et al., Journal of Labelled Compds. & Radiopharmaceuticals, vol. 39, pp. 677-684 (1997).
Hoffer et al., J. Med. Chem., vol. 17(9) pp. 1019-1020 (1974).
Ohba et al. Chem. Pharm. Bull. vol. 42, pp. 1784-1790 (1994).
Kulkarni et al., Aust. J. Chem. vol. 40(8) pp. 1399-1413 (1987).

(Continued)

*Primary Examiner* — David K O'Dell
(74) *Attorney, Agent, or Firm* — George W. Johnston; Patricia S. Rocha-Tramaloni; Kimberly J. Prior

(57) ABSTRACT

The present invention relates to diazole derivatives of the general formula

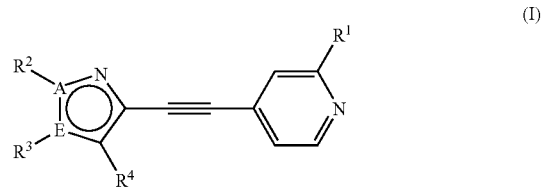

(I)

wherein A, E, $R^1$, $R^2$ and $R^3$ are as defined in application and pharmaceutical compositions containing them. The invention also relates to use of such compounds for the treatment of diseases mediated by the metabotropic glutamate receptors (mGluR), such as anxiety, chronic and acute pain, protection against liver damage, urinary incontinence, obesity, Fragile-X and autism, Alzheimer's disease, epilepsy, schizophrenia, ischemia, Huntington's chorea, amyotrophic lateral sclerosis (ALS), dementia caused by AIDs, and Parkinson's disease.

12 Claims, No Drawings

OTHER PUBLICATIONS

Vasileuskii et al., Bull. Acad. Sci. USSR Div. Chem. Sci. pp. 626-628 (1983).
Laronde et al., Inorg. Chim. Acta, vol. 296(1), pp. 208-221 (1999).
Shafiee et al., J. Heterocyclic Chem. vol. 33, pp. 671-673 (1996).
Shafiee et al., J. Heterocyclic Chem. vol. 35, pp. 607-610 (1998).
Ivanova et al. Chem. Heterocycl. Comp. vol. 36(2), pp. 262-264 (2000).
Wadsworth, G. H., J. Chem. Soc. vol. 57, p. 11 (1890).
Cornforth & Cookson, J. Chem. Soc. pp. 1085-1087 (1952).
Ross et al., J. Med. Chem. vol. 15(10) pp. 1035-1040 (1972).
Kiyomori et al., Tetrahedron Lett. vol. 40: p. 2657-2660 (1999).
Tohda et al., Synthesis p. 777-778 (1977).
Cliff et al., Synthesis pp. 681-682 (1994).
Ohira, Synth. Comm. 19: pp. 561-564 (1989).
Collman et al., Org. Lett. 2: p. 1233-1236 (2000).
Schlaeger & Christensen, Cytotechnology 30:71-83 (1999).
Porter et al., Br. J. Pharmacol. 128: pp. 13-20 (1999).
Millan, Progress in Neurobiology 70: pp. 83-244 (2003).
Abstract corresponding to DE 2035905, 1972.
Fabrizio Gasparini et al, Neuropharmacology Pergamon Press, XP001032948, vol. 38, No. 10 pp. 1493-1503 (1999).
Will P.J.M. Spooren et al, Trends in Phrmacological Sciences, Elsevier Trends Journal, XP004247865, vol. 22, No. 7, pp. 331-337 (2001).
Arena, et al., Journal of Medicinal Chem. American Chem. Society, XP001005697, vol. 18, No. 11, pp. 1147-1150 (1975).
Mutel, Expert Opin. Ther. Patents, vol. 12, p. 1845-1852 (2002).
Storto et al., European Journal of Pharmacology (2004), vol. 497(1) pp. 25-27.
Storto et al., Journal of Hepatology (2003) vol. 38(2), pp. 179-187.
Storto et al., Hepatology (Philadelphia) (2000), vol. 31(3), pp. 649-655.
Lynch, et al., Expert Opin. Ther. Patents (2002) vol. 12, pp. 11-27.
Pozharskii et al., Heterocycles in Life and Society, Wiley, pp. 1-6 (1997).
Alagille et al., Bioorganic & Medicinal Chemistry vol. 13 pp. 197-209 (2005).
Matos et al., Journal of Organic Chemistry vol. 63 pp. 461-470 (1998).
Dorwald, F. A., Side Reactions in Organic Synthesis, Wiley, pp. 279-308 (2005).
Tretyakov et al., Journal of the Chemical Society Perkin Transactions vol. 1, pp. 3713-3720 (1999).
Bing et al., Bioorganic & Medicinal Chemistry Letters vol. 12, pp. 2141-2144 (2002).
Nakamura, T., Bioorganic & Medicinal Chemistry letters vol. 14 pp. 333-336 (2004).
Patani, G. A., Chemical Reviews vol. 96 pp. 3147-3176 (1996).

DIAZOLE DERIVATIVES

PRIORITY TO RELATED APPLICATIONS

This application is a continuation of U.S. application Ser. No. 11/141,547, filed May 31, 2005, now pending; which claims the benefit of PCT/EP2004/005881 filed Jun. 1, 2004 and European Application No. 04021216.9 filed Sep. 7, 2004. The entire contents of the above-identified applications are hereby incorporated by reference.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

Selective mGluR5 antagonists are especially useful for the treatment of anxiety and pain.

SUMMARY OF THE INVENTION

The invention provides diazole derivatives of formula I

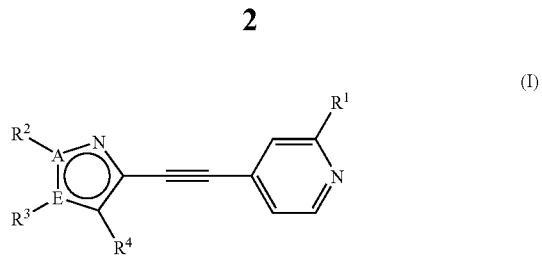

wherein
one of A or E is N and the other is C;
$R^1$ is halogen or cyano;
$R^2$ is lower alkyl;
$R^3$ is aryl or heteroaryl, each of which is optionally substituted by
one, two or three substituents selected from the group consisting of halogen, lower alkyl, lower alkoxy, cycloalkyl, lower haloalkyl, lower haloalkoxy, cyano, and NR'R", or by
1-morpholinyl, or by
1-pyrrolidinyl, optionally substituted by $(CH_2)_m OR$, or by
piperidinyl, optionally substituted by $(CH_2)_m OR$, or by
1,1-dioxo-thiomorpholinyl or by
piperazinyl, optionally substituted by lower alkyl or $(CH_2)_m$-cycloalkyl;
R is hydrogen, lower alkyl or $(CH_2)_m$-cycloalkyl;
R' and R" are each independently hydrogen, lower alkyl, $(CH_2)_m$-cycloalkyl or $(CH_2)_n OR$;
m is 0 or 1;
n is 1 or 2; and
$R^4$ is $CHF_2$, $CF_3$, $C(O)H$, or $CH_2 R^5$ wherein $R^5$ is hydrogen, OH, $C_1$-$C_6$-alkyl or $C_3$-$C_{12}$-cycloalkyl;
and pharmaceutically acceptable salts thereof. The present invention also provides methods of the production of such compounds and their pharmaceutically acceptable salts.

Moreover the invention provides pharmaceutical compositions containing one or more compounds of the present invention and pharmaceutically acceptable excipients and methods for manufacturing such compositions.

It has now surprisingly been found that compounds of formula I are metabotropic glutamate receptor antagonists. Compounds of formula I are distinguished by having valuable therapeutic properties. They can be used in the treatment or prevention of mGluR5 receptor mediated disorders. As such, the invention also provides a method for the treatment of mGluR5 receptor mediated disorders. In particular, the invention provides methods for the treatment of anxiety and chronic or acute pain, protection against liver damage or failure whether drug or disease induced. The invention further provides methods for the treatment of Alzheimer's disease, senile dementia, Parkinson's disease, Huntington's chorea, amyotrophic lateral sclerosis, multiple sclerosis, and schizophrenia.

DETAILED DESCRIPTION OF THE INVENTION

The following definitions of general terms used in the present description apply irrespective of whether the terms in question appear alone or in combination.

The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "lower alkoxy" denotes a lower alkyl residue in the sense of the foregoing definition bound via an oxygen atom. Examples of "lower alkoxy" residues include methoxy, ethoxy, isopropoxy and the like.

The term "halogen" denotes fluorine, chlorine, bromine and iodine.

The term "lower haloalkoxy" denotes lower alkoxy group as defined above which is substituted by one or more halogen. Examples of lower haloalkoxy include but are not limited to methoxy or ethoxy, substituted by one or more Cl, F, Br or I atom(s) as well as those groups specifically illustrated by the examples herein below. Preferred lower haloalkoxy are difluoro- or trifluoro-methoxy or ethoxy.

The term "lower haloalkyl" denotes a lower alkyl group as defined above which is substituted by one or more halogen. Examples of lower haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred lower haloalkyl are difluoro- or trifluoro-methyl or ethyl.

"Aryl" represents an aromatic carbocyclic group consisting of one individual ring, or one or more fused rings in which at least one ring is aromatic in nature. Preferred aryl group is phenyl.

The term "heteroaryl" refers to an aromatic 5- or 6-membered ring containing one or more heteroatoms selected from nitrogen, oxygen or sulphur. Preferred are those heteroaryl groups selected from nitrogen. Examples of such heteroaryl groups are pyridinyl, pyrazinyl, pyrimidinyl or pyridazinyl.

The term "cycloalkyl" denotes a saturated carbocyclic group, containing 3-12 carbon atoms, preferably 3-6 carbon atoms.

The term "pharmaceutically acceptable," such as pharmaceutically acceptable carrier, excipient, etc. means pharmacologically acceptable and substantially non-toxic to the subject to which the particular compound is administered.

The term "pharmaceutically acceptable salt" refers to any salt derived from an inorganic or organic acid or base. Such salts include: acid addition salts formed with inorganic acids such as hydrochloric acid, hydrobromic acid, sulfuric acid, nitric acid, phosphoric acid; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid or trimethylacetic acid.

The term "therapeutically effective amount" means an amount that is effective to prevent, alleviate or ameliorate symptoms of disease or prolong the survival of the subject being treated.

The invention provides compounds of formula I

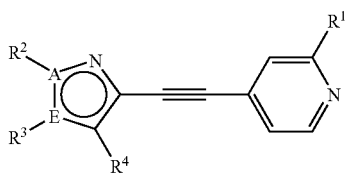

(I)

wherein
one of A or E is N and the other is C;
$R^1$ is halogen or cyano;

$R^2$ is lower alkyl;

$R^3$ is aryl or heteroaryl, each of which is optionally substituted by one, two or three substituents selected from the group consisting of halogen, lower alkyl, lower alkoxy, cycloalkyl, lower haloalkyl, lower haloalkoxy, cyano, and NR'R", or by 1-morpholinyl, or by 1-pyrrolidinyl, optionally substituted by $(CH_2)_m OR$, or by piperidinyl, optionally substituted by $(CH_2)_m OR$, or by 1,1-dioxo-thiomorpholinyl or by piperazinyl, optionally substituted by lower alkyl or $(CH_2)_m$-cycloalkyl;

R is hydrogen, lower alkyl or $(CH_2)_m$-cycloalkyl;

R' and R" are each independently hydrogen, lower alkyl, $(CH_2)_m$-cycloalkyl or $(CH_2)_n OR$;

m is 0 or 1;

n is 1 or 2;

$R^4$ is $CHF_2$, $CF_3$, $C(O)H$, or $CH_2R^5$ wherein $R^5$ is hydrogen, OH, $C_1$-$C_6$-alkyl or $C_3$-$C_{12}$-cycloalkyl;

and pharmaceutically acceptable salts thereof. The present invention also provides methods of the production of such compounds and their pharmaceutically acceptable salts.

Preferred compounds of formula I are those compounds of formulae Ia and Ib:

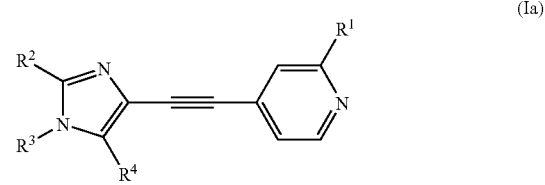

(Ia)

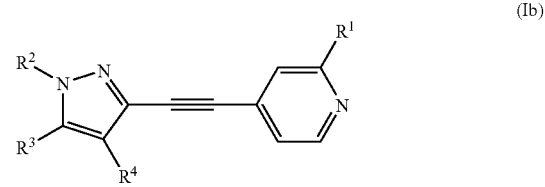

(Ib)

wherein $R^1$, $R^2$, $R^3$ and $R^4$ are as defined herein above.

In the compounds of formulae I, Ia or Ib, according to the invention, preferred compounds are those where $R^1$ is halogen, alternatively preferred compounds are those where $R^1$ is chloro or cyano.

In another embodiment, compounds in which $R^2$ is methyl or i-propyl are preferred.

In another embodiment, compounds wherein $R^3$ is selected from phenyl, pyridinyl, pyrazinyl, pyrimidinyl or pyridazinyl which may be substituted by one or more chloro, fluoro, lower alkyl, lower alkoxy, cyano, lower haloalkyl, lower haloalkoxy or cycloalkyl are preferred.

In another embodiment, compounds wherein $R^4$ is lower alkyl, $CHF_2$ or $CH_2OH$ and preferably methyl are preferred.

Preferred compounds are those compounds of formulae Ia and Ib

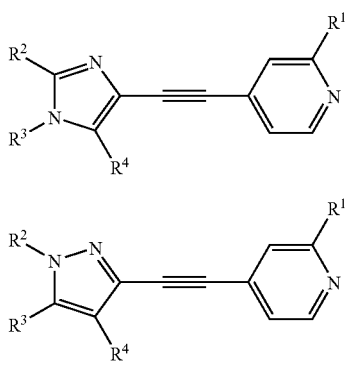

wherein
R¹ is halogen or cyano, preferably chloro or cyano;
R² is methyl or i-propyl;
R³ is selected from phenyl, pyridinyl, pyrazinyl, pyrimidinyl and pyridazinyl which may be substituted by one, two, or three chloro, fluoro, lower alkyl, lower alkoxy, cyano, lower haloalkyl, lower haloalkoxy or cycloalkyl; and
R⁴ is $CHF_2$ or $CH_2R^5$ wherein R⁵ is hydrogen, OH or $C_1$-$C_6$-alkyl wherein R⁴ is methyl is preferred;
and pharmaceutically acceptable salts thereof.

Preferred are those compounds of formula Ia, wherein, R³ is unsubstituted or substituted heteroaryl, wherein the substitution is selected from chloro, fluoro, $CF_3$, and lower alkyl, for example the following compounds:
2-[4-(2-Chloro-pyridin-4-ylethynyl)-2,5-dimethyl-1H-imidazol-1-yl]-5-methyl-pyridine;
2-Chloro-5-[4-(2-Chloro-pyridin-4-ylethynyl)-2,5-dimethyl-1H-imidazol-1-yl]-pyridine;
2-[4-(2-Chloro-pyridin-4-ylethynyl)-2,5-dimethyl-1H-imidazol-1-yl]-6-methyl-4-trifluoromethyl-pyridine;
2-[4-(2-Chloro-pyridin-4-ylethynyl)-2,5-dimethyl-1H-imidazol-1-yl]-pyrazine;
2-[4-(2-Chloro-pyridin-4-ylethynyl)-2,5-dimethyl-1H-imidazol-1-yl]-6-methyl-pyridine;
2-[4-(2-Chloro-pyridin-4-ylethynyl)-2,5-dimethyl-1H-imidazol-1-yl]-6-(trifluoromethyl)-pyridine; and
3-[4-(2-Chloro-pyridin-4-ylethynyl)-2,5-dimethyl-1H-imidazol-1-yl]-5-fluoro-pyridine.

Especially preferred are further those compounds of formula Ia, wherein, R³ is aryl, substituted by one, two, or three chloro, fluoro, $CF_3$, lower alkyl, lower alkoxy, $CF_3O$, and 1-morpholinyl, for example the following compounds:
2-Chloro-4-[1-(4-fluoro-phenyl)-2,5-dimethyl-1H-imidazol-4-ylethynyl]-pyridine;
2-Chloro-4-[1-(2,4-difluoro-phenyl)-2,5-dimethyl-1H-imidazol-4-ylethynyl]-pyridine;
2-Chloro-4-[1-(3,5-difluoro-phenyl)-2,5-dimethyl-1H-imidazol-4-ylethynyl]-pyridine;
2-Chloro-4-[1-(4-fluoro-2-methyl-phenyl)-2,5-dimethyl-1H-imidazol-4-ylethynyl]-pyridine;
2-Chloro-4-[1-(4-fluoro-3-methyl-phenyl)-2,5-dimethyl-1H-imidazol-4-ylethynyl]-pyridine;
2-Chloro-4-(2,5-dimethyl-1-p-tolyl-1H-imidazol-4-ylethynyl)-pyridine;
2-Chloro-4-[1-(3-chloro-4-methyl-phenyl)-2,5-dimethyl-1H-imidazol-4-ylethynyl]-pyridine;
2-Chloro-4-[1-(3-fluoro-4-methoxy-phenyl)-2,5-dimethyl-1H-imidazol-4-ylethynyl]-pyridine;
2-Chloro-4-[1-(4-methoxy-phenyl)-2,5-dimethyl-1H-imidazol-4-ylethynyl]-pyridine;
2-Chloro-4-[2,5-dimethyl-1-(4-trifluoromethoxy-phenyl)-1H-imidazol-4-ylethynyl]-pyridine;
2-Chloro-4-[2,5-dimethyl-1-(3-trifluoromethoxy-phenyl)-1H-imidazol-4-ylethynyl]-pyridine;
2-Chloro-4-[2,5-dimethyl-1-(4-trifluoromethyl-phenyl)-1H-imidazol-4-ylethynyl]-pyridine;
2-Chloro-4-[2,5-dimethyl-1-(3-methyl-4-trifluoromethoxy-phenyl)-1H-imidazol-4-ylethynyl]-pyridine;
2-Chloro-4-[1-(4-chloro-phenyl)-2,5-dimethyl-1H-imidazol-4-ylethynyl]-pyridine;
2-Chloro-4-[1-(3-chloro-2-fluoro-phenyl)-2,5-dimethyl-1H-imidazol-4-ylethynyl]-pyridine;
2-Chloro-4-[2,5-dimethyl-1-(3-trifluoromethyl-phenyl)-1H-imidazol-4-ylethynyl]-pyridine;
2-Chloro-4-[1-(3-chloro-4-fluoro-phenyl)-2,5-dimethyl-1H-imidazol-4-ylethynyl]-pyridine;
2-Chloro-4-[2,5-dimethyl-1-(2-methyl-4-trifluoromethoxy-phenyl)-1H-imidazol-4-ylethynyl]-pyridine;
2-Chloro-4-[5-difluoromethyl-1-(4-fluoro-phenyl)-2-methyl-1H-imidazol-4-ylethynyl]-pyridine;
[5-(2-Chloro-pyridin-4-ylethynyl)-3-(4-fluoro-phenyl)-2-methyl-3H-imidazol-4-yl]-methanol;
2-Chloro-4-[1-(4-methoxy-3-trifluoromethyl-phenyl)-2,5-dimethyl-1H-imidazol-4-ylethynyl]-pyridine;
2-Chloro-4-[1-(3,5-difluoro-4-methoxy-phenyl)-2,5-dimethyl-1H-imidazol-4-ylethynyl]-pyridine;
2-Chloro-4-[1-(4-methoxy-3-trifluoromethoxy-phenyl)-2,5-dimethyl-1H-imidazol-4-ylethynyl]-pyridine;
2-Chloro-4-[1-(3-methoxy-4-trifluoromethoxy-phenyl)-2,5-dimethyl-1H-imidazol-4-ylethynyl]-pyridine;
4-{3-[4-(2-Chloro-pyridin-4-ylethynyl)-2,5-dimethyl-imidazol-1-yl]-5-fluoro-phenyl}-morpholine;
2-Chloro-4-[1-(4-fluoro-2-trifluoromethoxy-phenyl)-2,5-dimethyl-1H-imidazol-4-ylethynyl]-pyridine;
2-Chloro-4-[1-(2-fluoro-4-trifluoromethoxy-phenyl)-2,5-dimethyl-1H-imidazol-4-ylethynyl]-pyridine;
2-Chloro-4-[2,5-dimethyl-1-(4-methyl-3-trifluoromethyl-phenyl)-1H-imidazol-4-ylethynyl]-pyridine;
2-Chloro-4-[2,5-dimethyl-1-(3-methyl-4-trifluoromethyl-phenyl)-1H-imidazol-4-ylethynyl]-pyridine;
2-Chloro-4-[2,5-dimethyl-1-(3-methyl-5-trifluoromethyl-phenyl)-1H-imidazol-4-ylethynyl]-pyridine;
2-Chloro-4-[1-(3-methoxy-5-trifluoromethyl-phenyl)-2,5-dimethyl-1H-imidazol-4-ylethynyl]-pyridine;
2-Chloro-4-[1-(3-methoxy-4-trifluoromethyl-phenyl)-2,5-dimethyl-1H-imidazol-4-ylethynyl]-pyridine;
2-Chloro-4-[1-(3,5-dichloro-phenyl)-2,5-dimethyl-1H-imidazol-4-ylethynyl]-pyridine;
2-Chloro-4-[1-(3-chloro-5-methyl-phenyl)-2,5-dimethyl-1H-imidazol-4-ylethynyl]-pyridine;
2-Chloro-4-[1-(3-fluoro-5-methyl-phenyl)-2,5-dimethyl-1H-imidazol-4-ylethynyl]-pyridine;
2-Chloro-4-[1-(3-chloro-5-methoxy-phenyl)-2,5-dimethyl-1H-imidazol-4-ylethynyl]-pyridine; and
2-Chloro-4-[1-(3-fluoro-5-methoxy-phenyl)-2,5-dimethyl-1H-imidazol-4-ylethynyl]-pyridine.

Still other preferred are those compounds of formula Ib, wherein R³ is aryl, substituted by one, two or three fluoro, especially the following compound: 2-Chloro-4-[5-(4-fluoro-phenyl)-1,4-dimethyl-1H-pyrazol-3-ylethynyl]-pyridine.

The compounds of formula Ia of the invention can be prepared according to various processes.

In one embodiment, the process of the invention comprises the following steps of reacting a compound of formula II

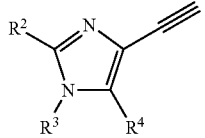
(II)

with a compound of formula III

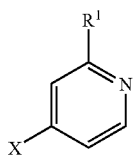
(III)

in order to obtain the compound of formula Ia;
wherein $R^1$, $R^2$, $R^3$ and $R^4$ are as defined above and X is halogen, and if desired, converting the compounds obtained into pharmaceutically acceptable acid addition salts. This process is described in more detail in scheme 1 and general procedure 1.

In another embodiment, the compounds of formula Ia can be prepared according to the following process of the invention which comprises the step of reacting a compound of formula IV

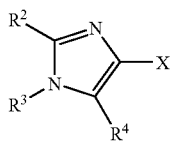
(IV)

with a compound of formula V

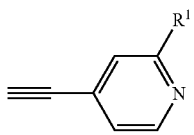
(V)

in order to obtain the compound of formula Ia;
wherein $R^1$, $R^2$, $R^3$ and $R^4$ are as defined above and X is halogen, and if desired, converting the compounds obtained into pharmaceutically acceptable acid addition salts. This process is described in more detail in scheme 2 and general procedure 2.

In still another embodiment, the compounds of formula Ia can be prepared according to the following process of the invention which comprises the step of reacting a compound of formula Ic

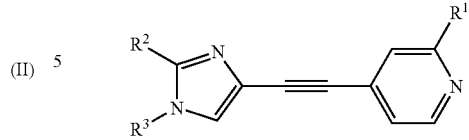
(Ic)

with a compound of formula VI $R^4$—X  (VI)

in order to obtain the compound of formula Ia;
wherein $R^1$, $R^2$, $R^3$ and $R^4$ are as defined above and X is halogen, and if desired, converting the compounds obtained into pharmaceutically acceptable acid addition salts. This process is described in more detail in scheme 3 and general procedure 3.

The compounds of formula Ib can be prepared according to the following process of the invention which comprises the step of reacting a compound of formula XXVI

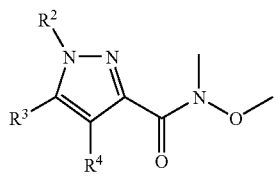
XXVI with a compound of formula XXVII

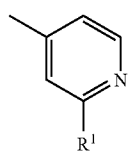
XXVII in order to obtain a compound of formula XXVIII

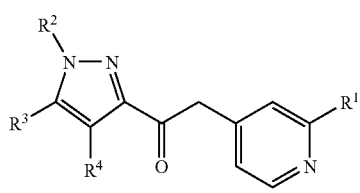
XXVIII and converting the compound of formula XXVIII into the compound of formula Ib;
wherein $R^1$, $R^2$, $R^3$ and $R^4$ are as defined above, and if desired, converting the compounds obtained into pharmaceutically acceptable acid addition salts. This process is described in more detail in scheme 4 and general procedure 4. In particular, the conversion of the compound of formula XXVIII into the compound of formula Ib is described in scheme 4 with steps 8 and 9.

The various processes of the invention are described in more detail in the following schemes with the following general procedures:
In these schemes, and unless specified otherwise, all starting materials are commercially available.

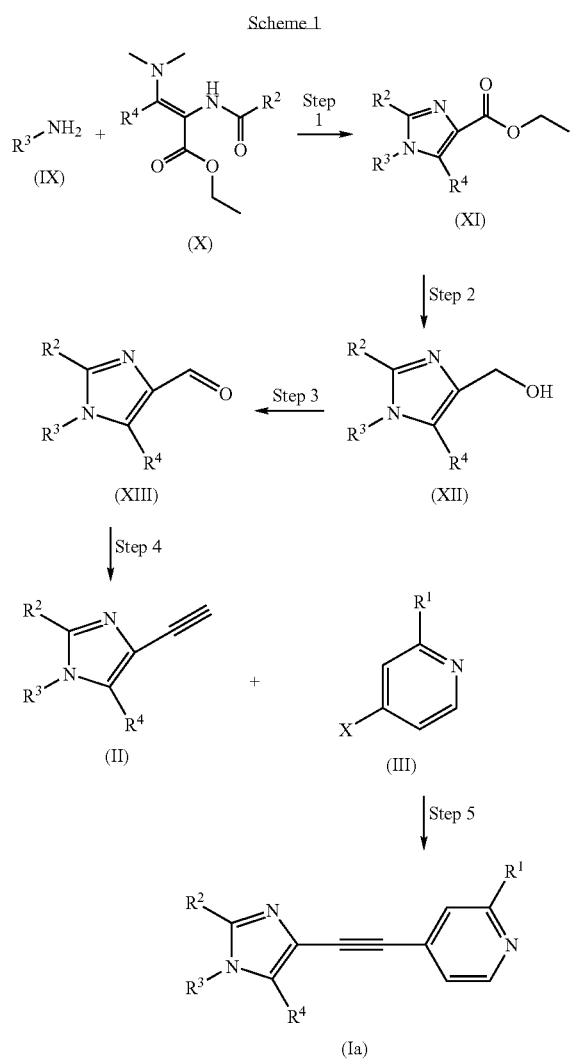

General Procedure 1

In the scheme 1, $R^1$, $R^2$, $R^3$ and $R^4$ are as defined hereinabove.

Step 1: Compound of Formula XI

The compound of formula X, which preparation is disclosed herein in the part synthesis of intermediates (see Example A), and compound IX are reacted at room temperature in the appropriate solvent (e.g. acetic acid). The crude product is isolated and purified by conventional methods.

Step 2: Compound of Formula XII

The compound of formula XI is dissolved in the appropriate solvent (e.g. dry THF) and cooled. The appropriate reducing agent is added (e.g. Lithium aluminum hydride).

Step 3: Compound of Formula XIII

The compound of formula XII is dissolved the appropriate solvent (e.g. dichloromethane) and the appropriate oxidizing agent is added (e.g. Mangan (IV)oxid).

Step 4: Compound of Formula II

The compound XIII is reacted with (1-Diazo-2-oxo-propyl)-phosphonic acid dimethyl ester. The crude product is isolated and purified by conventional methods.

Step 5: Compound of Formula Ia

The compound of formula II is reacted with the compound of formula III with the appropriate catalysts (e.g. Triphenylphosphine, bis(triphenylphosphine)palladium(II)chloride and Copper(I)iodide). The crude product is isolated and purified by conventional methods.

Scheme 1 and general procedure 1 are further illustrated in the section examples herein.

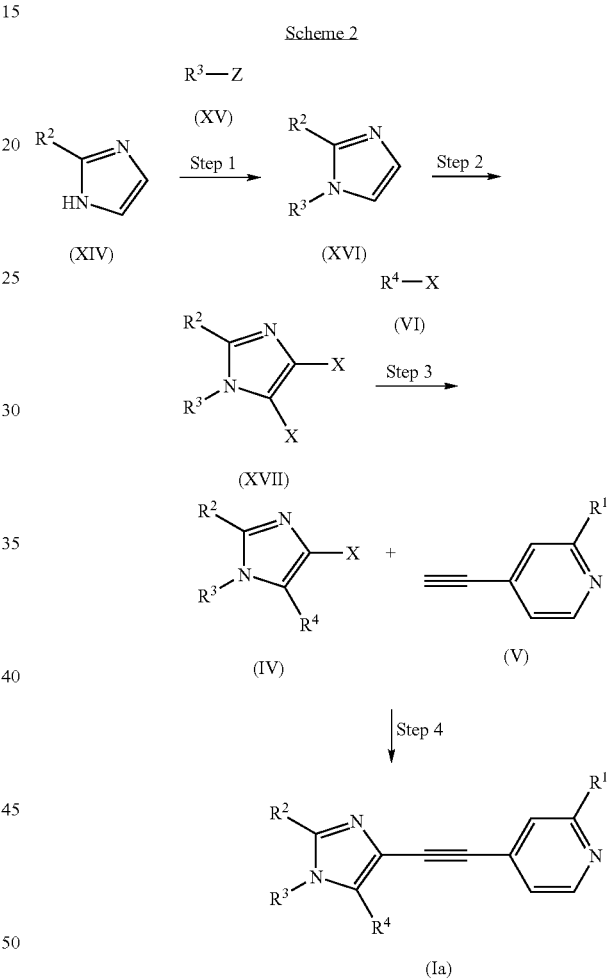

General Procedure 2

In the scheme 2, $R^1$, $R^2$, $R^3$ and $R^4$ are as defined hereinabove.

Step 1: Compound of Formula XVI

The compound of formula XIV is reacted with a compound of formula XV (Z is preferably $B(OH)_2$) with the appropriate catalyst (e.g. $[Cu(OH)TMEDA]_2Cl_2$ (1.13 g, 2 mmol)).

Step 2: Compound of Formula XVII

The compound of formula XVI is reacted with the appropriate halogen X (e.g. Iodine in Iodic acid, acetic acid, and concentrated sulfuric acid in water with carbon tetrachloride) and stirred over night. The crude product is isolated and purified by conventional methods.

Step 3: Compound of Formula IV

The compound of formula XVII is reacted with the compound of formula VI wherein X is halogen (e.g. iodomethane). The crude product is purified by conventional methods.

Step 4: Compound of Formula Ia

Solution 1: the compound of formula IV, which preparation is disclosed herein in the part synthesis of intermediates (see Example C) and the compound of formula V are mixed under inert gas (e.g. argon).

Solution 2: The appropriate catalyst mixture is prepared under inert gas (e.g. triphenylphosphine, bis(triphenylphosphine)-palladium(II)chloride, copper(I)iodide and triethyl amine in THF).

Solutions 1 and 2 are mixed under heating (e.g. 40° C.) and stirred. The crude product is purified by conventional methods.

Scheme 2 and general procedure 2 are further illustrated in the section examples herein.

Scheme 3

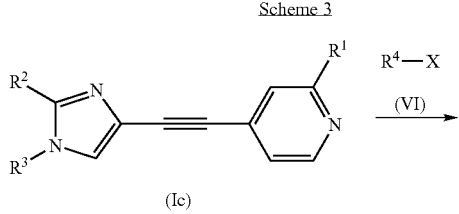

General Procedure 3

In the scheme 3, $R^1$, $R^2$, $R^3$ and $R^4$ are as defined hereinabove.

The compound of formula Ic is reacted with the compound of formula VI wherein X is halogen (e.g. iodomethane). The crude product is purified by conventional methods. The compounds of formula Ic can be prepared as described in WO 2004/108701.

Scheme 3 and general procedure 3 are further illustrated in the section examples herein.

Scheme 4

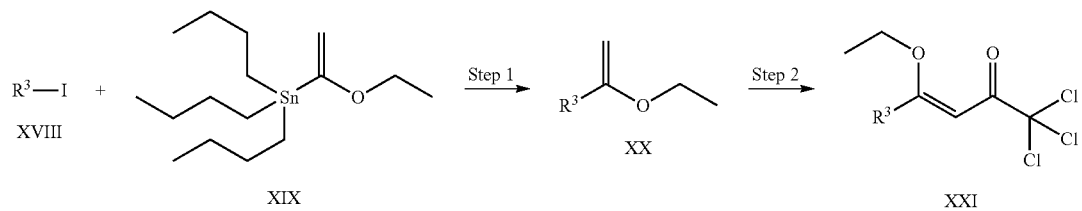

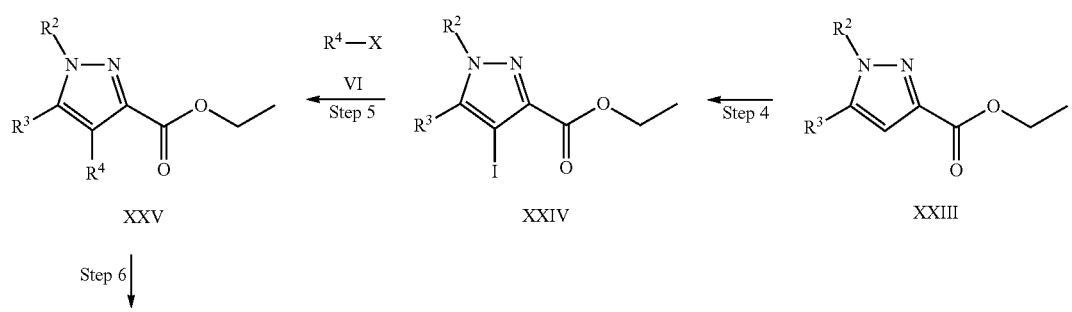

-continued

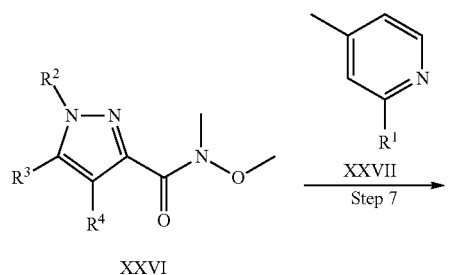

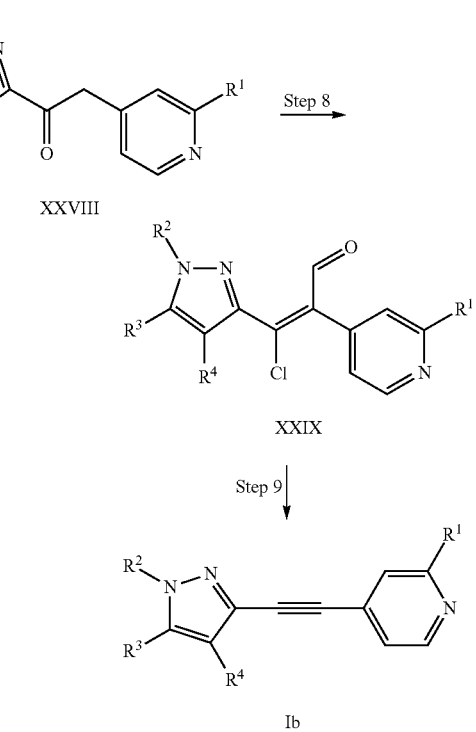

General Procedure 4

In the scheme 4, $R^1$, $R^2$, $R^3$ and $R^4$ are as defined hereinabove.

Step 1: Compound of Formula XX

A solution of the compound of formula XVIII and of the compound of formula XIX are reacted with the appropriate catalyst (e.g. 1-Ethoxyvinyltributyltin and Tetrakis(triphenylphosphine)Palladium in 130 ml of Toluene) The crude product is used directly in the next step.

Step 2: Compound of Formula XXI

A solution of the compound of formula XX (e.g. in pyridine) is added to Trichloroacetyl chloride. The product of formula XXI is obtained by conventional work up.

Step 3: Compound of Formula XXIII

A solution of the compound of formula XXI (e.g. in ethanol) is added to a solution of the compound of formula XII. The compound of formula XXIII is obtained by conventional work up.

Step 4: Compound of Formula XXIV

To a well stirred solution of the compound of formula XXIII (e.g. in Acetonitrile) are added Iodine and Cerium ammonium nitrate. The compound of formula XXIV is obtained by conventional work up.

Step 5: Compound of Formula XXV

To a solution of compound of formula XXIV (e.g. in dry THF) is added a solution of n-Butyllithium in THF. The compound of formula VI is then added (X is halogen). The product of formula XXV is obtained by conventional work up.

Step 6: Compound of Formula XXVI

To a suspension of N,O-Dimethylhydroxylamine ethyl ester (e.g. in dry methylene chloride) is added a solution of Trimethylaluminium (e.g. in Heptane). Then a solution of the compound of formula XXV is added (e.g. in dry methylene chloride). The product of formula XXVI is obtained by conventional work up.

Step 7: Compound of Formula XXVIII

A solution of sodium-bis(trimethylsilyl)amide (e.g. in THF) is added to the compound of formula XXVII (e.g. in dry THF). Then a solution of the compound of formula XXVI (e.g. in dry THF) is added. The product of formula XXVIII is obtained by conventional work up.

Step 8: Compound of Formula XXIX

To dry Methylene chloride is added Chloromethylene-dimethylimidium chloride. Then a solution of compound of formula XXVIII (e.g. in dry methylene chloride) is added. The product of formula XXIX is obtained by conventional work up.

Step 9: Compound of Formula Ib

To Potassium tert-butylate (e.g. in THF and water is added a solution of the compound of formula XXIX (e.g. in THF). The desired product of formula Ib is obtained by conventional work up.

Scheme 4 and general procedure 4 are further illustrated in the section examples herein.

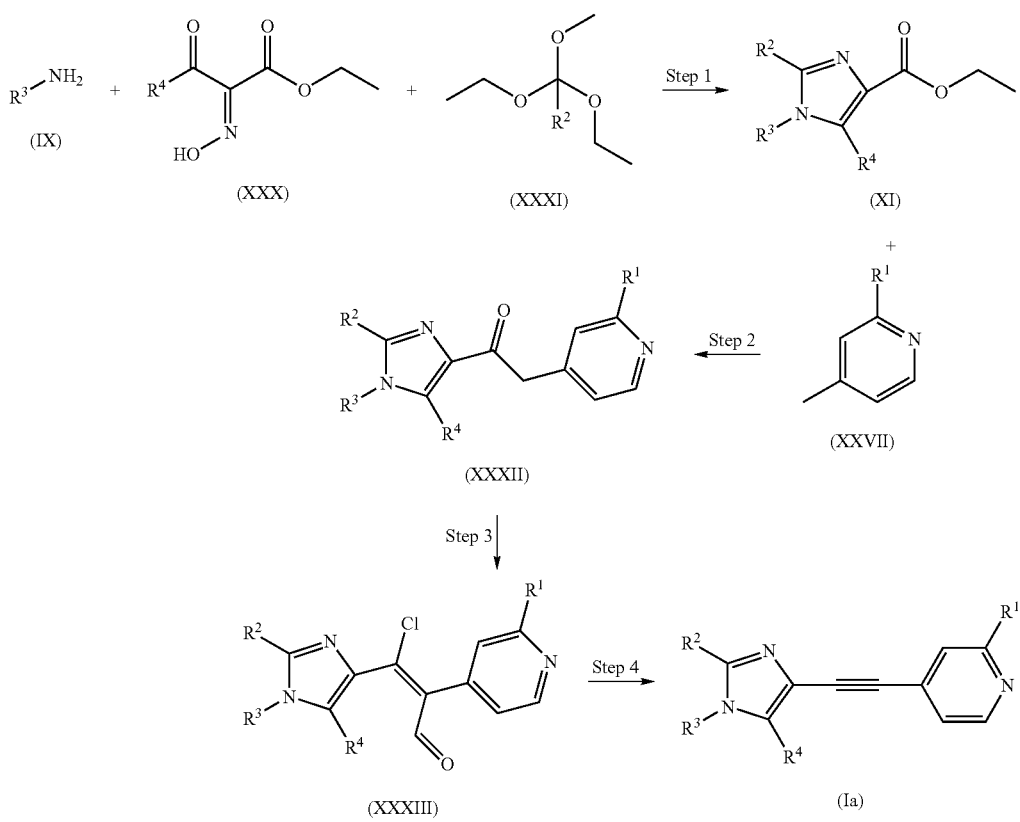

General Procedure 5

In the scheme 5, $R^1$, $R^2$, $R^3$ and $R^4$ are as defined hereinabove.

Step 1: Compound of Formula XI

The compound of formula XXX, which preparation is disclosed herein in the part synthesis of intermediates (see Example C), and compound IX are reacted at room temperature or higher temperature in the appropriate solvent (e.g. toluene). The crude product is concentrated and reacted with a compound of formula XXXI under hydrogen atmosphere in the presence of palladium to form a compound of formula XI which is isolated and purified by conventional methods.

Step 2: Compound of Formula XXXII

A solution of sodium-bis(trimethylsilyl)amide (e.g. in THF) is added to the compound of formula XXVII (e.g. in dry THF). Then a solution of the compound of formula XI (e.g. in dry THF) is added. The product of formula XXXII is obtained by conventional work up.

Step 3: Compound of Formula XXXIII

To dry methylene chloride is added chloromethylene-dimethylimidium chloride. Then a solution of compound of formula XXXII (e.g. in dry methylene chloride) is added. The product of formula XXXIII is obtained by conventional work up.

Step 4: Compound of Formula Ib

To Potassium tert-butylate (e.g. in THF and water is added a solution of the compound of formula XXXIII (e.g. in THF). The desired product of formula Ib is obtained by conventional work up.

Scheme 5 and general procedure 5 are further illustrated in the section examples herein. Pharmaceutically acceptable salts of compounds of formulae I, Ia and Ib can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formulae I, Ia and Ib and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

Other treatable indications are protection against liver damage, failure whether drug or disease induced, urinary incontinence, obesity, Fragile-X or Autism.

In addition, it is proposed that mGlu5 receptor antagonists protect against liver damage/failure whether drug or disease induced.

Storto, Marianna; Battaglia, Giuseppe; Gradini, Roberto; Bruno, Valeria; Nicoletti, Ferdinando; Vairetti, Mariapia. Mouse hepatocytes lacking mGlu5 metabotropic glutamate receptors are less sensitive to hypoxic damage. European Journal of Pharmacology (2004), 497(1), 25-27.

Storto, Marianna; Ngomba, Richard Teke; Battaglia, Giuseppe; Freitas, Isabel; Griffini, Patrizia; Richelmi, Plinio; Nicoletti, Ferdinando; Vairetti, Mariapia. Selective blockade of mGlu5 metabotropic glutamate receptors is protective against acetaminophen hepatotoxicity in mice. Journal of Hepatology (2003), 38(2), 179-187.

Storto, Marianna; De Grazia, Ugo; Knopfel, Thomas; Canonico, Pier Luigi; Copani, Agata; Richelmi, Plinio; Nicoletti, Ferdinando; Vairetti, Mariapia. Selective blockade of mGlu5 metabotropic glutamate receptors protects rat hepatocytes against hypoxic damage. Hepatology (Philadelphia) (2000), 31(3), 649-655.

The compounds of formula I, Ia and Ib and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method: For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 µg protein/well.

Saturation isotherms were determined by addition of twelve [$^3$H]MPEP concentrations (0.04-100 nM) to these membranes (in a total volume of 200 ηl) for 1 h at 4° C. Competition experiments were performed with a fixed concentration of [$^3$H]MPEP (2 nM) and $IC_{50}$ values of test compounds evaluated using 11 concentrations (0.3-10,000 nM). Incubations were performed for 1 hat 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 µM MPEP. The radioactivity on the filter was counted (3 min) on a Packard Top-count microplate scintillation counter with quenching correction after addition of 45 µl of microscint 40 (Canberra Packard S.A., Zürich, Switzerland) and shaking for 20 min.

For functional assays, [$Ca^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 µM final concentration). [$Ca^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using iterative non linear curve fitting software (Xcel fit). For binding experiments the Ki values of the compounds tested are given. The Ki value is defined by the following formula:

$$K_i = IC_{50}/[1+L/K_d]$$

in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

The compounds of the present invention are mGluR 5a receptor antagonists. The activities of compounds of formulae I, Ia and Ib as measured in the assay described above and as presented in the table hereafter are in the range of $K_i$<250 nM.

| Example | Ki (nM) |
|---|---|
| 1 | 39 |
| 2 | 40 |
| 13 | 14 |
| 26 | 6 |
| 27 | 42 |
| 28 | 211 |

The present invention also provides pharmaceutical compositions containing compounds of the invention, for example, compounds of formulae I, Ia, Ib and pharmaceutically acceptable salts thereof and a pharmaceutically acceptable excipient. Such pharmaceutical compositions can be in the form of tablets, coated tablets, dragées, hard and soft gelatine capsules, solutions, emulsions or suspensions. The pharmaceutical compositions also can be in the form of suppositories, or injectable solutions.

The pharmaceutical compositions of the invention, in addition to one or more compounds of the invention, contain a pharmaceutically acceptable excipient. Suitable pharmaceutically acceptable excipients include pharmaceutically inert, inorganic or organic carriers. Lactose, corn starch or derivatives thereof, talc, stearic acid or its salts and the like can be used, for example, as such as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable salts thereof and, if desired, one or more other therapeutically valuable substances into a galenical dosage form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injectable solutions.

Compounds of the present invention are selective mGluR antagonists. Therefore, the present invention also provides methods of treating diseases that are mediated by mGluR. Such methods include administering a therapeutically effective amount of a compound of the invention, for example, a compound of formula I, or a pharmaceutically acceptable salt thereof, to a patient in need of such treatment. Thus, in one embodiment, the invention provides a method for the treatment of a disease selected from the group consisting of anxiety, chronic and acute pain, protection against liver damage, urinary incontinence, obesity, Fragile-X and autism which comprises administering to an individual a therapeutically effective amount of a compound of formula I. In another embodiment, the invention provides a method for the treatment of a disease selected from the group consisting of Alzheimer's disease, epilepsy, schizophrenia, ischemia, Huntington's chorea, amyotrophic lateral sclerosis (ALS), dementia caused by AIDs, and Parkinson's disease comprising administering to an individual a therapeutically effective amount of a compound of formula I.

The dosages at which the compound of the invention is administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

Example 1

2-Chloro-4-[1-(4-fluoro-phenyl)-2,5-dimethyl-1H-imidazol-4-ylethynyl]-pyridine (Prepared According to General Procedure 3)

The title compound can be prepared according to general procedure 1 or general procedure 3. The preparation of the title compound according to general procedure 3 is described hereafter in example 1 and the preparation of the title compound according to general procedure 1 is described in example 3.

This compound was prepared according to the general procedure 3 described hereinabove. 2-chloro-4-[1-(4-fluoro-phenyl)-2-methyl-1H-imidazol-4-ylethynyl]-pyridine (200 mg, 0.607 mmol) was dissolved in 10 mL THF and cooled to −75° C. Lithiumdiisopropylamide (0.45 ml, 0.91 mmol) was added, and the mixture stirred for 15 min at −75° C. Iodomethane (0.05 ml, 0.85 mmol) was added and stirring was continued at −75° C. for 2 hrs. The reaction mixture was quenched with sat. $NaHCO_3^-$ solution and extracted with water and ethyl acetate. The combined organic extracts were dried with sodium sulfate, filtered and evaporated. The crude product was purified by flash chromatography on silica gel (heptane/ethylacetate 90:10→20:80 gradient) and by recrystallization from ethyl acetate. The desired compound was obtained as a white solid (40 mg, 19%), MS: m/e=326.5 (M+H$^+$).

Example 2

2-Chloro-4-[1-(2,4-difluoro-phenyl)-2,5-dimethyl-1H-imidazol-4-ylethynyl]-pyridine This compound was prepared according to the general procedure 1 described hereinabove.

Step 1: 1-(2,4-Difluoro-phenyl)-2,5-dimethyl-1H-imidazole-4-carboxylic acid ethyl ester (Z)-2-Acetylamino-3-dimethylamino-but-2-enoic acid ethyl ester (5.5 g, 26 mmol) (Example A) and 2,4-Difluoroaniline (3.3 g, 26 mmol) were stirred at room temperature in acetic acid (45 ml) for 2 hrs. The reaction mixture was evaporated under vacuum at 40° C. to obtain 10.3 g dark brown solid [(Z)-2-Acetylamino-3-(2,4-difluoro-phenylamino)-but-2-enoic acid ethyl ester] [MS: m/e=299.2 (M+H+)], which was refluxed over night at 145° C. with fine powdered ammonium sulfate (0.17 g, 1 mmol) in hexamethyldisilazane (64 ml, 306 mmol). The reaction mixture was slowly cooled to 0-5° C. The precipitated solid was filtered and washed with n-hexane to obtain the desired compound as a light brown crystalline solid (1.76 g, 25%), MS: m/e=281.1 (M+H+).

Step 2: [1-(2,4-Difluoro-phenyl)-2,5-dimethyl-1H-imidazol-4-yl]-methanol 1-(2,4-Difluoro-phenyl)-2,5-dimethyl-1H-imidazole-4-carboxylic acid ethyl ester (0.5 g, 2 mmol) was dissolved in 15 mL dry THF and cooled to 0° C. Lithium aluminum hydride (2.0 mL, 1M in THF, 2 mmol) was added dropwise and stirred for 45 min at 0° C. The reaction mixture was quenched successively with 76 µl water, 76 µl 15% sodium hydroxide and 230 µl water. Sodium sulfate was added, stirred for 10 min, filtered and evaporated to dryness to obtain the desired compound as a white solid (0.39 g, 92%), MS: m/e=239.2 (M+H+).

Step 3: 1-(2,4-Difluoro-phenyl)-2,5-dimethyl-1H-imidazole-4-carbaldehyde

[1-(2,4-Difluoro-phenyl)-2,5-dimethyl-1H-imidazol-4-yl]-methanol (0.38 g, 1.6 mmol) was dissolved in 35 ml dichloromethane. Mangan(IV)oxid (1.38 g, 16 mmol) was added, and the reaction mixture stirred at reflux for 2 hrs. The suspension was filtered through a dicalite speed plus pad and washed with dichloromethane. The solvents were evaporated, and the desired compound was obtained as a yellow oil (0.325 g, 86%), MS: m/e=237.1 (M+H+).

Step 4: 1-(2,4-Difluoro-phenyl)-4-ethynyl-2,5-dimethyl-1H-imidazole

Diazo-2-oxo-propyl)-phosphonic acid dimethyl ester (0.37 g, 2 mmol) was dissolved in 20 mL methanol. Potassium carbonate (0.38 g, 3 mmol) was added. A solution of 1-(2,4-Difluoro-phenyl)-2,5-dimethyl-1H-imidazole-4-carbaldehyde (0.32 g, 1 mmol) in 5 ml methanol was added drop wise at room temperature. The reaction mixture was stirred at room temperature overnight. The solvent was evaporated. The residue was taken up in 15 ml water and extracted three times with ethyl acetate (15 ml each). The combined organic extracts were dried with sodium sulfate, filtered and evaporated. The crude product was purified by flash chromatography on silica gel (heptane/ethyl acetate 90:10→50:50 gradient) and the desired compound was obtained as a light yellow solid (0.165 g, 52%), MS: m/e=233.1 (M+).

Step 5: 2-Chloro-4-[1-(2,4-difluoro-phenyl)-2,5-dimethyl-1H-imidazol-4-ylethynyl]-pyridine 2-Chloro-4-iodo-pyridine (0.21 g, 1 mmol) was dissolved in 10 mL of dry THF and 0.29 mL triethyl amine. This mixture was evacuated and backfilled with argon several times to remove oxygen from the solution. Triphenylphosphine (5 mg, 0.03 eq) and bis(triphenylphosphine)palladium (II)chloride (24 mg, 0.05 eq) were added, and the reaction mixture was stirred at room temperature for 10 min. 1-(2,4-Difluoro-phenyl)-4-ethynyl-2,5-dimethyl-1H-imidazole (0.16 g, 1 mmol) and Copper(I)iodide (3 mg, 0.02 eq) were added. The reaction mixture was stirred at room temperature overnight. The solvent was evaporated. The residue was taken up in 10 mL water and extracted three times with ethyl acetate (10 mL each). The combined organic extracts were dried with magnesium sulfate, filtered and evaporated. The crude product was purified by chromatography on silica gel (n-heptane/ethyl acetate 1:1) and recrystallized from diethyl ether. The desired product was obtained as a white solid (0.1 g, 42%), MS: m/e=344.0 (M+).

Example 3

2-Chloro-4-[1-(4-fluoro-phenyl)-2,5-dimethyl-1H-imidazol-4-ylethynyl]-pyridine (Prepared According to General Procedure 1)

The title compound, MS: m/e=326.2 (M+H+), was prepared in accordance with the general method of example 2 (procedure 1) from (Z)-2-Acetylamino-3-dimethylamino-but-2-enoic acid ethyl ester and 4-Fluoroaniline.

Example 4

2-Chloro-4-[1-(3,5-difluoro-phenyl)-2,5-methyl-1H-imidazol-4-ylethynyl]-pyridine The title compound, MS: m/e=344.0 (M+H+), was prepared in accordance with the general method of example 2 (procedure 1) from (Z)-2-Acetylamino-3-dimethylamino-but-2-enoic acid ethyl ester and 3,5-Difluoroaniline.

Example 5

2-Chloro-4-[1-(4-fluoro-2-methyl-phenyl)-2,5-dimethyl-1H-imidazol-4-ylethynyl]-pyridine The title compound, MS: m/e=340.0 (M+H+), was prepared in accordance with the general method of example 2 (procedure 1) from (Z)-2-Acetylamino-3-dimethylamino-but-2-enoic acid ethyl ester and 4-Fluoro-2-methylaniline.

Example 6

2-Chloro-4-[1-(4-fluoro-3-methyl-phenyl)-2,5-dimethyl-1H-imidazol-4-ylethynyl]-pyridine The title compound, MS: m/e=340.0 (M+H+), was prepared in accordance with the general method of example 2 (procedure 1) from (Z)-2-Acetylamino-3-dimethylamino-but-2-enoic acid ethyl ester and 4-Fluoro-3-methylaniline.

Example 7

2-Chloro-4-(2,5-dimethyl-1-p-tolyl-1H-imidazol-4-ylethynyl)-pyridine

This compound was prepared according to the general procedure 3 as described hereinabove. 2-Chloro-4-(2-methyl-1-p-tolyl-1H-imidazol-4-ylethynyl)-pyridine (220 mg, 0.71 mmol) was dissolved in 5 mL THF and cooled to −75° C. Lithiumdiisopropylamide (0.61 ml, 1.22 mmol) was added, and the mixture stirred for 15 min at −75° C. Iodomethane (0.08 ml, 1.14 mmol) was added and stirring was continued at −75° C. for 2 hrs. The reaction mixture was quenched with sat. $NaHCO_3^-$ solution and extracted with water and ethyl acetate. The combined organic extracts were dried with sodium sulfate, filtered and evaporated. The crude product was purified by flash chromatography on silica gel (heptane/ethylacetate 90:10→0:100 gradient) and by recrystallization from dichloromethane and diisopropylether. The desired compound was obtained as a light yellow solid (30 mg, 13%), MS: m/e=322.3 (M+H+).

Example 8

2-Chloro-4-[1-(3-chloro-4-methyl-phenyl)-2,5-dimethyl-1H-imidazol-4-ylethynyl]-pyridine The title compound, MS: m/e=356.1 (M+H+), was prepared in accordance with the general method of example 2 (procedure 1) from (Z)-2-Acetylamino-3-dimethylamino-but-2-enoic acid ethyl ester and 3-Chloro-4-methylaniline.

Example 9

2-Chloro-4-[1-(3-fluoro-4-methoxy-phenyl)-2,5-dimethyl-1H-imidazol-4-ylethynyl]-pyridine The title compound, MS: m/e=356.1 (M+H+), was prepared in accordance with the general method of example 2 (procedure 1) from (Z)-2-Acetylamino-3-dimethylamino-but-2-enoic acid ethyl ester and 2-Fluoro-p-anisidine.

Example 10

2-Chloro-4-[1-(4-methoxy-phenyl)-2,5-dimethyl-1H-imidazol-4-ylethynyl]-pyridine

The title compound, MS: m/e=338.1 (M+H+), was prepared in accordance with the general method of example 2

(procedure 1) from (Z)-2-Acetylamino-3-dimethylamino-but-2-enoic acid ethyl ester and p-Anisidine.

Example 11

2-Chloro-4-[2,5-dimethyl-1-(4-trifluoromethoxy-phenyl)-1H-imidazol-4-ylethynyl]-pyridine The title compound, MS: m/e=392.1 (M+H+), was prepared in accordance with the general method of example 2 (procedure 1) from (Z)-2-Acetylamino-3-dimethylamino-but-2-enoic acid ethyl ester and 4-(Trifluoromethoxy)aniline.

Example 12

2-Chloro-4-[2,5-dimethyl-1-(3-trifluoromethoxy-phenyl)-1H-imidazol-4-ylethynyl]-pyridine The title compound, MS: m/e=392.1 (M+H+), was prepared in accordance with the general method of example 2 (procedure 1) from (Z)-2-Acetylamino-3-dimethylamino-but-2-enoic acid ethyl ester and 3-(Trifluoromethoxy)aniline.

Example 13

2-Chloro-4-[2,5-dimethyl-1-(4-trifluoromethyl-phenyl)-1H-imidazol-4-ylethynyl]-pyridine This compound was prepared according to the general procedure 2 as described hereinabove.

Step 1:
2-Methyl-1-(4-trifluoromethyl-phenyl)-1H-imidazole

2-Methylimidazole (1.0 g, 12 mmol) was dissolved in 35 mL THF. 4-(Trifluoromethyl)phenylboronic acid (2.66 g, 14 mmol) and [Cu(OH)TMEDA]$_2$Cl$_2$ (1.13 g, 2 mmol) were added. Oxygen was bubbled through the reaction mixture for 30 minutes and stirring was continued at room temperature overnight. The reaction mixture was filtered through a dicalite speed plus pad, washed with 80 ml THF and evaporated. The crude product was purified by flash chromatography on silica gel with ethyl acetate. The desired compound was obtained as a light yellow solid (1.6 g, 58%), MS: m/e=227.2 (M+H+).

Step 2: 4,5-Diiodo-2-methyl-1-(4-trifluoromethyl-phenyl)-1H-imidazole

A mixture of 2-Methyl-1-(4-trifluoromethyl-phenyl)-1H-imidazole (1.6 g, 7.1 mmol), Iodine (2.15 g, 8.5 mmol), Iodic acid (0.75 g, 4.2 mmol), 25 ml acetic acid, 2.5 ml 30% sulfuric acid in water and 4 ml carbon tetrachloride was stirred over night at 80° C. The reaction mixture was cooled to room temperature, decolorized with 5% NaHSO$_3^-$ solution and basified to pH 9 with sodium hydroxide. Water was added and extracted two times with 50 ml ethyl acetate. The organic layers were washed with Brine, dried with sodium sulfate and evaporated. The crude product was recrystallized with little ethyl acetate and cyclohexane. The desired product was obtained as a light yellow solid (1.05 g, 31%). MS: m/e=479.0 (M+).

Step 3: 4-Iodo-2,5-dimethyl-1-(4-trifluoromethyl-phenyl)-1H-imidazole 4,5-Diiodo-2-methyl-1-(4-trifluoromethyl-phenyl)-1H-imidazole (1.0 g, 2.1 mmol) was dissolved in 15 ml THF and cooled to −75° C. n-Butyllithium (1.6M in Hexane) (1.60 ml, 2.5 mmol) was added, and the mixture stirred for 60 min at −75° C. Iodomethane (0.19 ml, 3.0 mmol) was added and stirring was continued 30 min. at −75° C. and then 1 h without dry ice bath. The reaction mixture was quenched with sat. NaHCO$_3^-$ solution and extracted with water and ethyl acetate. The combined organic extracts were dried with sodium sulfate, filtered and evaporated. The crude product was purified by flash chromatography on silica gel (heptane/ethylacetate 100:0→60:40 gradient) and by recrystallization from little ethyl acetate and cyclohexane. The desired compound was obtained as a white solid (197 mg, 26%), MS: m/e=367.0 (M+H$^+$).

Step 4: 2-Chloro-4-[2,5-dimethyl-1-(4-trifluoromethyl-phenyl)-1H-imidazol-4-ylethynyl]-pyridine Solution 1: 2-Chloro-4-trimethylsilanylethynyl-pyridine (144 mg, 0.69 mmol) (Example B) and 4-Iodo-2,5-dimethyl-1-(4-trifluoromethyl-phenyl)-1H-imidazole (180 mg, 0.49 mmol) were dissolved in 3 ml dry THF. This mixture was evacuated and backfilled with argon several times to remove oxygen from the solution.

Solution 2: Triphenylphosphine (4 mg, <0.1 mmol), bis (triphenylphosphine)-palladium(II)chloride (21 mg, <0.1 mmol), copper(I)iodide (3 mg, <0.1 mmol) and triethyl amine (0.1 ml, 0.71 mmol) were dissolved in 4 ml dry THF. This mixture was also evacuated and backfilled with argon several times to remove oxygen from the solution.

Solution 2 was heated to 40° C., and solution 1 was added dropwise. The reaction mixture was heated to 60° C. and tetrabutylammonium fluoride solution (1M in THF, 0.7 ml, 0.7 mmol) was added drop wise. The reaction was then stirred 2 hrs at 60° C. The residue was taken up in 15 ml water and extracted two times with ethyl acetate (15 ml each). The combined organic extracts were dried with magnesium sulfate, filtered and evaporated. The crude product was purified by chromatography on silica gel (heptane/ethyl acetate 1:1) and recrystallized from little ethyl acetate and caclohexane. The desired product was obtained as a white solid (95 mg, 51%), MS: m/e=376.3 (M+H$^+$).

Example 14

2-Chloro-4-[2,5-dimethyl-1-(3-methyl-4-trifluoromethoxy-phenyl)-1H-imidazol-4-ylethynyl]-pyridine The title compound, MS: m/e=406.2 (M+H+), was prepared in accordance with the general method of example 13 (procedure 2) from 2-Methylimidazole and 3-Methyl-4-(trifluoromethoxy)phenylboronic acid (prepared from 4-Bromo-2-methyl-1-trifluoromethoxy-benzene).

Example 15

2-[4-(2-Chloro-pyridin-4-ylethynyl)-2,5-dimethyl-1H-imidazol-1-yl]-5-methyl-pyridine Step 1:
5-Methyl-2-(2-methyl-imidazol-1-yl)-pyridine 2-Methylimidazole (2.0 g, 24 mmol) and 2-Fluoro-5-methylpyridine (5.41 g, 49 mmol) were dissolved in 40 ml dimethyl formamide. Cesium carbonate (23.8 g, 73 mmol) was added, and the reaction mixture was stirred at 100° C. overnight. The reaction mixture was poured into 100 mL water and extracted three times with ethyl acetate (150 mL each). The combined organic extracts were dried with sodium sulfate, filtered and evaporated. The desired compound was obtained as a brown oil (4.0 g, 95%), MS: m/e=174.1 (M+H+).

Step 2: 2-[4-(2-Chloro-pyridin-4-ylethynyl)-2,5-dimethyl-imidazol-1-yl]-5-methyl-pyridine The title compound, MS: m/e=323.3 (M+H+), was prepared in accordance with the general method of example 13, step 2, 3 and 4 (procedure 2) from 5-Methyl-2-(2-methyl-imidazol-1-yl)-pyridine.

Example 16

2-Chloro-5-[4-(2-Chloro-pyridin-4-ylethynyl)-2,5-dimethyl-1H-imidazol-1-yl]-pyridine The title compound, MS: m/e=344.1 (M+H+), was prepared in accordance with the general method of example 2 (procedure 1) from (Z)-2-Acetylamino-3-dimethylamino-but-2-enoic acid ethyl ester and 5-Amino-2-chloropyridine.

Example 17

2-[4-(2-Chloro-pyridin-4-ylethynyl)-2,5-dimethyl-1H-imidazol-1-yl]-6-methyl-4-trifluoromethyl-pyridine The title compound, MS: m/e=391.1 (M+H+), was prepared in accordance with the general method of example 15 from 2-Methylimidazole and 2-Chloro-6-methyl-4-(trifluoromethyl)-pyridine.

Example 18

2-[4-(2-Chloro-pyridin-4-ylethynyl)-2,5-dimethyl-1H-imidazol-1-yl]-pyrazine

The title compound, MS: m/e=310.2 (M+H+), was prepared in accordance with the general method of example 15, step 1 and example 12, step 4 from 5-Iodo-2,4-dimethyl-1H-imidazole (see synthesis of intermediates, example C) and 2-Chloropyrazine.

Example 19

2-Chloro-4-[1-(4-chloro-phenyl)-2,5-dimethyl-1H-imidazol-4-ylethynyl]-pyridine

The title compound, MS: m/e=342.1 (M+H+), was prepared in accordance with the general method of example 13 (procedure 2) from 2-Methylimidazole and 4-Chlorophenyl-boronic acid.

Example 20

2-Chloro-4-[1-(3-chloro-2-fluoro-phenyl)-2,5-dimethyl-1H-imidazol-4-ylethynyl]-pyridine The title compound, MS: m/e=360.1 (M+H+), was prepared in accordance with the general method of example 2 (procedure 1) from (Z)-2-Acetylamino-3-dimethylamino-but-2-enoic acid ethyl ester and 3-Chloro-2-fluoroaniline.

Example 21

2-Chloro-4-[2,5-dimethyl-1-(3-trifluoromethyl-phenyl)-1H-imidazol-4-ylethynyl]-pyridine The title compound, MS: m/e=376.3 (M+H+), was prepared in accordance with the general method of example 13 (procedure 2) from 2-Methylimidazole and 3-(Trifluoromethyl)phenylboronic acid.

Example 22

2-Chloro-4-[1-(3-chloro-4-fluoro-phenyl)-2,5-dimethyl-1H-imidazol-4-ylethynyl]-pyridine The title compound, MS: m/e=360.0 (M+H+), was prepared in accordance with the general method of example 2 (procedure 1) from (Z)-2-Acetylamino-3-dimethylamino-but-2-enoic acid ethyl ester and 3-Chloro-4-fluoroaniline.

Example 23

2-[4-(2-Chloro-pyridin-4-ylethynyl)-2,5-dimethyl-1H-imidazol-1-yl]-6-methyl-pyridine The title compound, MS: m/e=323.3 (M+H+), was prepared in accordance with the general method of example 15 from 2-Methylimidazole and 2-Chloro-6-methyl-pyridine.

Example 24

2-[4-(2-Chloro-pyridin-4-ylethynyl)-2,5-dimethyl-1H-imidazol-1-yl]-6-(trifluoromethyl)-pyridine The title compound, MS: m/e=377.1 (M+H+), was prepared in accordance with the general method of example 15 from 2-Methylimidazole and 2-Chloro-6-trifluoromethylpyridine.

Example 25

2-Chloro-4-[2,5-dimethyl-1-(2-methyl-4-trifluoromethoxy-phenyl)-1H-imidazol-4-ylethynyl]-pyridine The title compound, was prepared in accordance with the general method of example 2 (procedure 1) from (Z)-2-Acetylamino-3-dimethylamino-but-2-enoic acid ethyl ester and 2-Methyl-4-(trifluoromethoxy) aniline.

Example 26

2-Chloro-4-[5-(4-fluoro-phenyl)-1,4-dimethyl-1H-pyrazol-3-ylethynyl]-pyridine

The title compound, was prepared in accordance with the general method of general procedure 4 and scheme 4.

Step 1: 1-(1-Ethoxy-vinyl)-4-fluoro-benzene

A solution of 10.0 g 4-Fluoro-iodobenzene, 21.1 g 1-Ethoxyvinyltributyltin and 2.6 g Tetrakis(triphenylphosphine)Palladium in 130 ml of Toluene was refluxed overnight under an argon atmosphere. The dark brown solution was filtered over filter aid and concentrated in vaccuo. The crude dark brown oil (7.49 g) was directly used in the next step.

Step 2: [1,1,1-Trichloro-4-ethoxy-4-(4-fluoro-phenyl)-but-3-en-2-one

A solution of 7.49 g 1-(1-Ethoxy-vinyl)-4-Fluorobenzene in 3.6 mL of Pyridine was added at 0° C. to 8.19 g of Trichloroacetyl chloride. The suspension was diluted with 15 ml of dry methylene chloride and stirred at room temperature overnight. The resulting dark brown suspension was concentrated in vaccuo, filtered over a silica gel column with a 9:1 mixture of Heptane and Ethyl acetate as eluant. One obtains after concentration 28 g of a reddish brown oil which was repurified by chromatography on silica gel using a 19:1 mixture of Heptane and Ethyl acetate as eluant. The obtained brown oil (10.15 g) was directly used in the next step.

Step 3: 5-(4-Fluoro-phenyl)-1-methyl-1H-pyrazole-3-carboxylic acid ethyl ester A solution of 10.15 g [1,1,1-Trichloro-4-ethoxy-4-(4-fluoro-phenyl)-but-3-en-2-one in 50 ml of Ethanol was added dropwise to a solution of 2.1 ml of Methylhydrazine and 4.7 ml of 9N HCl/EtOH in 250 ml of Ethanol. The reaction mixture was stirred at reflux for 2 hrs. The yellow solution was allowed to cool and concentrated in vaccuo. The residue was taken up in 200 ml of Methylene chloride. The organic phase was washed successively with 1N HCl solution and water. After drying over Magnesium sulfate and concentration, the crude product (8.56 g) was purified by chromatography over silica gel using a 2:1 mixture of Heptane and Ethyl acetate as eluant. The solvents were evaporated, and the desired compound was obtained as a yellow oil (2.79 g, 35%), which solidified on standing, MS: m/e=249.1 ([M+1]$^+$).

Step 4: 5-(4-Fluoro-phenyl)-4-iodo-1-methyl-1H-pyrazole-3-carboxylic acid ethyl ester To a well stirred solution of 2.79 g of 5-(4-Fluoro-phenyl)-1-methyl-1H-pyrazole-3-carboxylic acid ethyl ester in 100 ml of Acetonitrile were added 1.71 g of Iodine and 3.70 g of Cerium ammonium nitrate. The mixture was stirred for 3 h at 50° C. The red solution was then allowed to cool and was concentrated in vaccuo. The residue was taken up in 200 ml of Ethyl acetate. The organic phase was successively washed with 5% Sodium bisulfite solution and brine. After drying over Magnesium sulfate and concentration, a beige solid 4.06 g (96%) was obtained which is sufficiently pure and was directly used in the next step. MS: m/e=375.3 ([M+1]$^+$).

Step 5: 5-(4-Fluoro-phenyl)-1,4-dimethyl-1H-pyrazole-3-carboxylic acid ethyl ester To a −78° C. solution of 4.06 g of 5-(4-Fluoro-phenyl)-4-iodo-1-methyl-1H-pyrazole-3-carboxylic acid ethyl ester in 80 mL of dry THF were added dropwise 8.13 ml of a 1.6 M solution of n-Butyllithium in THF maintaining the temperature below −70° C. The solution was stirred for 15 min at −75° C. and 1.4 ml of Methyl iodide was added. The reaction mixture was stirred for 30 min at −75° C. and allowed to warm up to room temperature. The mixture was worked up with Ethyl acetate and brine. The combined organic extracts were dried with magnesium sulfate, filtered and evaporated. The crude product (3.15 g) was purified by chromatography on silica gel (Heptane/Ethyl acetate 2:1). The desired product was obtained as a yellow oil (1.00 g, 35%), which solidified on standing. MS: m/e=263.1 ([M+1]+).

Step 6: 5-(4-Fluoro-phenyl)-1,4-dimethyl-1H-pyrazole-3-carboxylic acid methoxymethyl-amide To a 0° C. cooled suspension of 0.54 g of N,O-Dimethylhydroxylamine ethyl ester in 10 mL of dry Methylene chloride were added dropwise 2.8 ml of a 2M solution of Trimethylaluminium in Heptane. The solution was stirred for 30 min at room temperature and then cooled to 0° C. Then a solution of 0.65 g 5-(4-Fluoro-phenyl)-1,4-dimethyl-1H-pyrazole-3-carboxylic acid ethyl ester in 4 ml of dry Methylene chloride was added dropwise at 0° C. The solution was allowed to warm up to room temperature and stirred for 3 h. The reaction mixture was cooled to 0° C. and 20 ml of water were added dropwise. The pH of the aqueous phase was adjusted to 7-8 with 1N Sodium hydroxide solution. The mixture was worked up with Methylene chloride and water. The combined organic extracts were dried with magnesium sulfate, filtered and evaporated. The crude product was purified by chromatography on silica gel (Heptane/Ethyl acetate 7:3). The desired product was obtained as a colorless oil (0.52 g, 68%), MS: m/e=278.0 ([M+1]+).

Step 7: 2-(2-Chloro-pyridin-4-yl)-1-[5-(4-fluoro-phenyl)-1,4-dimethyl-1H-pyrazol-3-yl]-ethanone To 10 ml of dry THF cooled to −65° C. were added 1.35 ml of a 2M solution of Sodium-bis(trimethylsilyl)amide in THF. Then a solution of 0.32 g 2-Chlor-4-methyl pyridine in 1 ml of dry THF was added dropwise maintaining the temperature at −70° C. for 30 min. Then a solution of 0.50 g of 5-(4-Fluoro-phenyl)-1,4-dimethyl-1H-pyrazole-3-carboxylic acid methoxymethyl-amide in 5 ml of dry THF was added dropwise over a 10 min period maintaining the temperature below −65° C. The solution was stirred for 2 h at −60° C., and then allowed to warm up to 0° C. and stirred for 20 min at this temperature. Then 0.31 ml of Acetic acid was added dropwise at −50° C., and the solution was allowed to warm up to room temperature and stirred overnight. The mixture was concentrated in vaccuo. The residue was taken up in Ethyl acetate. The organic phase was washed with saturated bicarbonate solution and brine, dried over magnesium sulfate, filtered and evaporated. The crude product (0.67 g, yellow oil) was purified by chromatography on silica gel (Heptane/Ethyl acetate 4:1). The desired product was obtained as a white solid (0.27 g, 70%), MS: m/e=344.0 ([M+1]+).

Step 8: 3-Chloro-2-(2-chloro-pyridin-4-yl)-3-[5-(4-fluoro-phenyl)-1,4-dimethyl-1H-pyrazol-3-yl]-propenal To 15 ml of dry Methylene chloride cooled to 0° C. was added 0.34 ml of Chloromethylene-dimethylimidium chloride. Then a solution of 0.35 g 2-(2-Chloro-pyridin-4-yl)-1-[5-(4-fluoro-phenyl)-1,4-dimethyl-1H-pyrazol-3-yl]-ethanone in 6 ml of dry Methylene chloride was added at 0° C. over a period of 5 min. The yellow suspension was stirred for 2.5 h at 0° C., and then diluted with 20 ml of Methylene chloride. The organic phase was washed with saturated bicarbonate solution and water, dried over magnesium sulfate, filtered and evaporated. The crude product (0.42 g, light yellow solid) was directly used in the next step, MS: m/e=389.1 (M+).

Step 9: 2-Chloro-4-[5-(4-fluoro-phenyl)-1,4-dimethyl-1H-pyrazol-3-ylethynyl]-pyridine To 11 ml of THF cooled to 0° C. were added 0.26 g of Potassium tert-butylate and 20 μl of water. Then a solution of 0.40 g 3-Chloro-2-(2-chloro-pyridin-4-yl)-3-[5-(4-fluoro-phenyl)-1,4-dimethyl-1H-pyrazol-3-yl]-propenal in 7 ml of THF was added at 0°. After stirring for 1 h at 5° C., 10 ml of 5% Bicarbonate solution were added and the aqueous phase was extracted twice with Ethyl acetate. The combined organic phases were washed with water and brine, dried over magnesium sulfate, filtered and evaporated. The crude product (0.28 g, yellow oil) was purified by chromatography on silica gel (Heptane/Ethyl acetate 4:1). The desired product was obtained as a white solid (0.275 g, 82%), MS: m/e=326.0 (M+).

Example 27

2-Chloro-4-[5-difluoromethyl-1-(4-fluoro-phenyl)-2-methyl-1H-imidazol-4-ylethynyl]-pyridine This compound was prepared according to the general procedure 3 described hereinabove.

Step 1: 5-(2-Chloro-pyridin-4-ylethynyl)-3-(4-fluoro-phenyl)-2-methyl-3H-imidazole-4-carbaldehyde 2-chloro-4-[1-(4-fluoro-phenyl)-2-methyl-1H-imidazol-4-ylethynyl]-pyridine (2.0 g, 6.42 mmol) was dissolved in 50 mL THF and cooled to −70° C. Lithiumdiisopropylamide 2M/THF (4.8 ml, 9.6 mmol) was added, and the mixture stirred for 15 min at −70° C. Dimethylformamide (0.69 ml, 9.0 mmol) was added and stirring was continued at −70° C. for 3 hrs. The reaction mixture was quenched with sat. NaHCO$_3^-$ solution and extracted with water and ethyl acetate. The combined organic extracts were dried with sodium sulfate, filtered and evaporated. The crude product was purified by flash chromatography on silica gel (heptane/ethylacetate 1:2). The desired compound was obtained as a yellow solid (220 mg, 10%), MS: m/e=340.0 (M+H$^+$).

Step 2: 2-Chloro-4-[5-difluoromethyl-1-(4-fluoro-phenyl)-2-methyl-1H-imidazol-4-ylethynyl]-pyridine To a solution of 100 mg (0.29 mmol) 5-(2-Chloro-pyridin-4-ylethynyl)-3-(4-fluoro-phenyl)-2-methyl-3H-imidazole-4-carbaldehyde in 3 ml of dry methylene chloride were added 125 mg (0.775 mmol) Diethylaminosulfur trifluoride (DAST). The mixture was stirred at room temperature for 3 days. The reaction mixture was quenched with sat. NaHCO$_3$— solution and extracted with water and methylene chloride. The combined organic extracts were dried with sodium sulfate, filtered and evaporated. The crude product was purified by flash chromatography on silica gel (heptane/ethyl acetate 1:1). The desired compound was obtained as a light yellow solid (47 mg, 44%), MS: m/e=362.1 (M+H$^+$).

Example 28

[5-(2-Chloro-pyridin-4-ylethynyl)-3-(4-fluoro-phenyl)-2-methyl-3H-imidazol-4-yl]-methanol To a solution of 100 mg (0.29 mmol) 5-(2-Chloro-pyridin-4-ylethynyl)-3-(4-fluoro-phenyl)-2-methyl-3H-imidazole-4-carbaldehyde (example 26) in 5 ml of methanol were added at 0° C. 11 mg (0.29 mmol) of sodium borohydride, and the mixture was stirred for 1 h at 0° C. The reaction mixture was quenched with sat. NaHCO$_3^-$ solution and evaporated. The residue was extracted with water and ethyl acetate. The combined organic extracts were dried with sodium sulfate, filtered and evaporated. The crude product was purified by flash chromatography on silica gel (heptane/ethyl acetate 1:1). The desired compound was obtained as a white solid (40 mg, 40%), MS: m/e=342.1 (M+H$^+$).

Example 29

2-Chloro-4-[1-(4-methoxy-3-trifluoromethyl-phenyl)-2,5-dimethyl-1H-imidazol-4-ylethynyl]-pyridine This compound was prepared according to the general procedure 5 described hereinabove.

Step 1: 1-(4-Methoxy-3-trifluoromethyl-phenyl)-2,5-dimethyl-1H-imidazole-4-carboxylic acid ethyl ester Ethyl 2-Hydroxyimino-3-oxobutanoate (1.67 g, 10.5 mmol) (Example C), 3-trifluoromethyl-4-methoxyaniline (2.0 g, 10.5 mmol) and pyridinium p-toluenesulfonate (0.13 g, 0.52 mmol) were stirred at 75° C. in toluene (15 ml) for 4 hrs. The reaction mixture was evaporated under vacuum at 40° C. The residue was dissolved in triethyl orthoacetate (14.3 ml, 78 mmol) and p-toluenesulfonic acid monohydrate (0.1 g, 0.52 mmol), and palladium on charcoal (0.6 g) were added. The reaction mixture was stirred for 4 hrs under hydrogen atmosphere. The dark suspension was filtered and evaporated to dryness. The crude product was recrystallized at 0° C. from TBME and n-heptane. The desired product was obtained as a light brown solid (1.28 g, 36%), MS: m/e=343.1 (M+H+).

Step 2: 2-(2-Chloro-pyridin-4-yl)-1-[1-(4-methoxy-3-trifluoromethyl-phenyl)-2,5-dimethyl-1H-imidazol-4-yl]-ethanone 1-(4-Methoxy-3-trifluoromethyl-phenyl)-2,5-dimethyl-1H-imidazole-4-carboxylic acid ethyl ester (0.8 g, 2.3 mmol) and 2-chloro-4-methylpyridine (0.36 g, 2.8 mmol) were dissolved in 10 mL toluene. This solution was dropped to a cold (0° C.) mixture of potassium bis(trimethylsilyl)amide (1.17 g, 5.84 mmol) in 15 mL toluene. The reaction mixture was stirred for 90 min. at 0° C. 0.4 mL acetic acid were added, and the mixture extracted with water, saturated NaHCO$_3$-Solution and brine. The aqueous layer was washed with toluene (100 mL). The combined organic extracts were dried with sodium sulfate and filtered. The solvent was evaporated, and the crude product [(0.8 g, 81%), [MS: m/e=424.5 (M+H+)] was used without any further purification for the next step.

Step 3: 3-Chloro-2-(2-chloro-pyridin-4-yl)-3-[1-(4-methoxy-3-trifluoromethyl-phenyl)-2,5-dimethyl-1H-imidazol-4-yl]-propenal A solution of 2-(2-Chloro-pyridin-4-yl)-1-[1-(4-methoxy-3-trifluoromethyl-phenyl)-2,5-dimethyl-1H-imidazol-4-yl]-ethanone (0.8 g, 1.9 mmol) in 8 mL dichloromethane was dropped to a cold (0° C.) suspension of chloromethylenedimethyliminium chloride (0.6 g, 4.7 mmol) in 4 mL dichloromethane. The reaction mixture was stirred at 0° C. for 1 hr. The reaction was diluted with 10 mL water and basified with saturated NaHCO$_3^-$ solution to pH 8. The layers were separated and the aqueous layer was extracted with 100 mL dichloromethane. The organic layers were washed with water, combined and dried over magnesium sulfate. The sol- Step 4: 2-Chloro-4-[1-(4-methoxy-3-trifluoromethyl-phenyl)-2,5-dimethyl-1H-imidazol-4-ylethynyl]-pyridine A solution of 3-Chloro-2-(2-chloro-pyridin-4-yl)-3-[1-(4-methoxy-3-trifluoromethyl-phenyl)-2,5-dimethyl-1H-imidazol-4-yl]-propenal (0.9 g, 1.9 mmol) in 8 mL THF was dropped to a cold (0° C.) suspension of potassium tert-butoxide (0.47 g, 4.2 mmol) in 4 mL THF and water (0.04 mL, 2.1 mmol). The light brown reaction mixture was stirred at 0° C. for 1 hr. The reaction was extracted two times with ethyl acetate, saturated NaHCO$_3^-$ solution, water and brine. The combined organic extracts were dried with sodium sulfate, filtered and evaporated. The crude product was purified by chromatography on silica gel (n-heptane/ethyl acetate 90:10→0:100) to obtain the desired product as a white solid (0.15 g, 19%), MS: m/e=406.2 (M+H+).

Example 30

2-Chloro-4-[1-(3,5-difluoro-4-methoxy-phenyl)-2,5-dimethyl-1H-imidazol-4-ylethynyl]-pyridine The title compound [MS: m/e=373.9 (M+H+)], was prepared in accordance with the general method of example 29 (general procedure 5) from Ethyl 2-Hydroxyimino-3-oxobutanoate (Example C) and 3,5-Difluoro-4-methoxyaniline (Example D).

Example 31

2-Chloro-4-[1-(4-methoxy-3-trifluoromethoxy-phenyl)-2,5-dimethyl-1H-imidazol-4-ylethynyl]-pyridine The title compound [MS: m/e=421.9 (M+H+)], was prepared in accordance with the general method of example 29 (general procedure 5) from Ethyl 2-Hydroxyimino-3-oxobutanoate (Example C) and 4-Methoxy-3-trifluoromethoxyaniline (Example E).

Example 32

2-Chloro-4-[1-(3-methoxy-4-trifluoromethoxy-phenyl)-2,5-dimethyl-1H-imidazol-4-ylethynyl]-pyridine The title compound [MS: m/e=421.9 (M+H+)], was prepared in accordance with the general method of example 29 (general procedure 5) from Ethyl 2-Hydroxyimino-3-oxobutanoate (Example C) and 3-Methoxy-4-trifluoromethoxyaniline (Example F).

Example 33

3-[4-(2-Chloro-pyridin-4-ylethynyl)-2,5-dimethyl-1H-imidazol-1-yl]-5-fluoro-pyridine The title compound, MS: m/e=327.0 (M+H+), was prepared in accordance with the general method of example 15 from 2-Methylimidazole and 3,5-difluoropyridine.

Example 34

4-{3-[4-(2-Chloro-pyridin-4-ylethynyl)-2,5-dimethyl-imidazol-1-yl]-5-fluoro-phenyl}-morpholine A mixture of 2-Chloro-4-[1-(3,5-difluoro-phenyl)-2,5-methyl-1H-imidazol-4-ylethynyl]-pyridine (0.08 g, 0.23 mmol) (Example 4), morpholine (0.041 g, 0.46 mmol) and potassium carbonate (0.13 g, 0.92 mmol) in 1 mL DMSO was stirred at 100° C. for 60 hrs. The reaction mixture was cooled and extracted two times with ethyl acetate and water. The organic layers were washed with brine, combined and dried over sodium sulfate. The solvent was evaporated and the crude product was purified by chromatography on silica gel (n-heptane/ethyl acetate 90:10→30:70) and recrystallized from diisopropylether to obtain the desired product as a white solid (8.0 mg, 8%), MS: m/e=411.2 (M+H+).

Example 35

2-Chloro-4-[1-(4-fluoro-2-trifluoromethoxy-phenyl)-2,5-dimethyl-1H-imidazol-4-ylethynyl]-pyridine The title compound, MS: m/e=410.0 (M+H+), was prepared in accordance with the general method of example 2 (procedure 1) from (Z)-2-Acetylamino-3-dimethylamino-but-2-enoic acid ethyl ester and 4-Fluoro-2-trifluoromethoxyaniline (Example G).

Example 36

2-Chloro-4-[1-(2-fluoro-4-trifluoromethoxy-phenyl)-2,5-dimethyl-1H-imidazol-4-ylethynyl]-pyridine The title compound, MS: m/e=410.1 (M+H+), was prepared in accordance with the general method of example 2 (procedure 1) from (Z)-2-Acetylamino-3-dimethylamino-but-2-enoic acid ethyl ester and 2-Fluoro-4-trifluoromethoxyaniline (Example H).

Example 37

The following examples can also be prepared as according to general procedure 1 or general procedure 5:
2-Chloro-4-[2,5-dimethyl-1-(4-methyl-3-trifluoromethyl-phenyl)-1H-imidazol-4-ylethynyl]-pyridine;
2-Chloro-4-[2,5-dimethyl-1-(3-methyl-4-trifluoromethyl-phenyl)-1H-imidazol-4-ylethynyl]-pyridine;
2-Chloro-4-[2,5-dimethyl-1-(3-methyl-5-trifluoromethyl-phenyl)-1H-imidazol-4-ylethynyl]-pyridine;
2-Chloro-4-[1-(3-methoxy-5-trifluoromethyl-phenyl)-2,5-dimethyl-1H-imidazol-4-ylethynyl]-pyridine;
2-Chloro-4-[1-(3-methoxy-4-trifluoromethyl-phenyl)-2,5-dimethyl-1H-imidazol-4-ylethynyl]-pyridine;
2-Chloro-4-[1-(3,5-dichloro-phenyl)-2,5-dimethyl-1H-imidazol-4-ylethynyl]-pyridine;
2-Chloro-4-[1-(3-chloro-5-methyl-phenyl)-2,5-dimethyl-1H-imidazol-4-ylethynyl]-pyridine;
2-Chloro-4-[1-(3-fluoro-5-methyl-phenyl)-2,5-dimethyl-1H-imidazol-4-ylethynyl]-pyridine;
2-Chloro-4-[1-(3-chloro-5-methoxy-phenyl)-2,5-dimethyl-1H-imidazol-4-ylethynyl]-pyridine; and 2-Chloro-4-[1-(3-fluoro-5-methoxy-phenyl)-2,5-dimethyl-1H-imidazol-4-ylethynyl]-pyridine;

Synthesis of Intermediates

Example A (Z)-2-Acetylamino-3-dimethylamino-but-2-enoic acid ethyl ester

In this example of the compound X, $R^2$ and $R^4$ are both methyl. Nevertheless, it is understood that the person skilled in the art would be able to prepare other compounds of formula X, wherein $R^2$ and $R^4$ are other than methyl using the method of the following example and commercially available starting materials:

Step 1: 4-[1-Dimethylamino-eth-(Z)-ylidene]-2-methyl-4H-oxazol-5-one

N-Acetylglycine (10.0 g, 85.4 mmol) and Phosphoroxychloride (19.6 ml, 213.5 mmol) were mixed and cooled to 5° C. N',N-Dimethylacetamide (19.7 ml, 213.5 mmol) was added drop-wise slowly during 30 min at 5-10° C. (exothermic!). The reaction mixture was stirred at 45° C. for 2 hrs and then cooled to room temperature. Dichloromethane (35 ml) was added, and the mixture poured into 200 ml ice-water. The pH was adjusted to pH 8 with ammonium hydroxide, and the mixture was extracted twice with 50 ml dichloromethane. The organic extracts were washed with 30 ml water, dried over magnesium sulfate, filtered and evaporated. The crude product was purified by column chromatography on silica gel (ethyl acetate), and the desired compound was obtained as a light brown solid (7.40 g, 51%), MS: m/e=169.2 (M+H+).

Step 2:
(Z)-2-Acetylamino-3-dimethylamino-but-2-enoic acid ethyl ester

4-[1-Dimethylamino-eth-(Z)-ylidene]-2-methyl-4H-oxazol-5-one (7.4 g, 44.0 mmol) was dissolved in ethanol (50 ml), and sodium hydride (0.10 g, 4.4 mmol) was added at room temperature. The dark solution was refluxed for 1 h. The solvent was evaporated, and the crude product [MS: m/e=215.5 (M+H+)] was used without any further purification for the next step.

Example B

5-Iodo-2,4-dimethyl-1H-imidazole

In this example of the compound XIX, $R^2$ is methyl, $R^4$ is methyl, and X is chloro. Nevertheless it is understood that the person skilled in the art would be able to prepare other compounds of formula XIX, wherein $R^2$ and $R^4$ are other than methyl, and X is other than chloro, using the method used for in the following example:

2,4-Dimethylimidazole (5.0 g, 52 mmol) was suspended in 100 ml Acetonitrile, and N-Iodosuccinimide (14.0 g, 62.4 mmol) was added. The reaction mixture was stirred at reflux for 16 hours, then evaporated and decolorized with sat $NaHSO_3^-$ solution. Water was added and extracted two times with 100 ml ethyl acetate. The organic layers were washed with Brine, dried with sodium sulfate and evaporated. The crude product was purified by chromatography on silica gel (dichloromethane/methanol 9:1). The desired product was obtained as a light brown solid (5.10 g, 44%), MS: m/e=223.0 (M+H+).

Example C

Ethyl 2-Hydroxyimino-3-oxobutanoate

The title compound was prepared from ethyl acetoacetate in accordance with the literature reference of Robinson, Stanislawski & Mulholland, The Journal of Organic Chemistry, Volume 66, Number 12, 4148-4152 (2001).

Example D 3,5-Difluoro-4-methoxyaniline

The title compound was prepared from 2,6-difluorophenol in accordance with the literature reference of Qiu, Stevenson, O'Beirne and Silverman, J. Med. Chem. 1999, 42, 329-332.

Example E

4-Methoxy-3-trifluoromethoxyaniline

The title compound can be prepared in accordance with patent WO 2004007444.

Example F

3-Methoxy-4-trifluoromethoxyaniline

The title compound can be prepared in accordance with patent WO 9613492.

Example G

4-Fluoro-2-trifluoromethoxyaniline

The title compound can be prepared in accordance with patent EP 318704.

Example H

2-Fluoro-4-trifluoromethoxyaniline

The title compound can be prepared in accordance with patent EP 318704.

Preparation of the Pharmaceutical Compositions

Example I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of the formula Ia

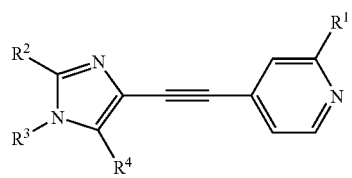

(Ia)

wherein
$R^1$ is halogen or cyano;
$R^2$ is lower alkyl;
$R^3$ is phenyl, pyridinyl, or a diazine optionally substituted by
one, two or three substituents selected from the group consisting of halogen, lower alkyl, lower alkoxy, cycloalkyl, lower haloalkyl, lower haloalkoxy, cyano, NR'R" or by
1-morpholinyl or by
1-pyrrolidinyl, optionally substituted by $(CH_2)_m OR$, or by piperidinyl, optionally substituted by $(CH_2)_m OR$, or by
1,1-dioxo-thiomorpholinyl or by
piperazinyl, optionally substituted by lower alkyl or $(CH_2)_m$-cycloalkyl;
R is hydrogen, lower alkyl or $(CH_2)_m$-cycloalkyl;
R' and R" are each independently hydrogen, lower alkyl, $(CH_2)_m$-cycloalkyl or $(CH_2)_n OR$;

m is 0 or 1;
n is 1 or 2; and
$R^4$ is $CHF_2$, $CF_3$, C(O)H, or $CH_2R^5$ wherein $R^5$ is hydrogen, OH, $C_1$-$C_6$-alkyl or $C_3$-$C_{12}$-cycloalkyl;
or a pharmaceutically acceptable salt thereof.

2. A compound according to claim 1, wherein
$R^1$ is halogen;
$R^2$ is methyl or i-propyl;
$R^3$ is selected from phenyl, pyridinyl, pyrazinyl, pyrimidinyl or pyridazinyl each of which is optionally substituted by one, two, or three chloro, fluoro, lower alkyl, lower alkoxy, cyano, lower haloalkyl, lower haloalkoxy or cycloalkyl; and
$R^4$ is $CHF_2$ or $CH_2R^5$ wherein $R^5$ is hydrogen, OH or $C_1$-$C_6$-alkyl;
or a pharmaceutically acceptable salt thereof.

3. A compound of formula Ia according to claim 1, wherein $R^3$ is pyridinyl or a diazine that is unsubstituted or substituted with a substituent selected from chloro, fluoro, $CF_3$, and lower alkyl.

4. A compound of formula Ia according to claim 3 which is selected from the group consisting of:
2-[4-(2-Chloro-pyridin-4-ylethynyl)-2,5-dimethyl-1H-imidazol-1-yl]-5-methyl-pyridine;
2-Chloro-5-[4-(2-Chloro-pyridin-4-ylethynyl)-2,5-dimethyl-1H-imidazol-1-yl]-pyridine;
2-[4-(2-Chloro-pyridin-4-ylethynyl)-2,5-dimethyl-1H-imidazol-1-yl]-6-methyl-4-trifluoromethyl-pyridine;
2-[4-(2-Chloro-pyridin-4-ylethynyl)-2,5-dimethyl-1H-imidazol-1-yl]-pyrazine;
2-[4-(2-Chloro-pyridin-4-ylethynyl)-2,5-dimethyl-1H-imidazol-1-yl]-6-methyl-pyridine;
2-[4-(2-Chloro-pyridin-4-ylethynyl)-2,5-dimethyl-1H-imidazol-1-yl]-6-(trifluoromethyl)-pyridine; and
3-[4-(2-Chloro-pyridin-4-ylethynyl)-2,5-dimethyl-1H-imidazol-1-yl]-5-fluoro-pyridine.

5. A compound of formula Ia according to claim 1, wherein $R^3$ is phenyl, substituted by one, two, or three chloro, fluoro, $CF_3$, lower alkyl, lower alkoxy, $CF_3O$ or 1-morpholinyl.

6. A compound of formula Ia in accordance with claim 5 which is selected from the group consisting of:
2-Chloro-4-[1-(4-fluoro-phenyl)-2,5-dimethyl-1H-imidazol-4-ylethynyl]-pyridine;
2-Chloro-4-[1-(2,4-difluoro-phenyl)-2,5-dimethyl-1H-imidazol-4-ylethynyl]-pyridine;
2-Chloro-4-[1-(3,5-difluoro-phenyl)-2,5-dimethyl-1H-imidazol-4-ylethynyl]-pyridine;
2-Chloro-4-[1-(4-fluoro-2-methyl-phenyl)-2,5-dimethyl-1H-imidazol-4-ylethynyl]-pyridine;
2-Chloro-4-[1-(4-fluoro-3-methyl-phenyl)-2,5-dimethyl-1H-imidazol-4-ylethynyl]-pyridine;
2-Chloro-4-(2,5-dimethyl-1-p-tolyl-1H-imidazol-4-ylethynyl)-pyridine;
2-Chloro-4-[1-(3-chloro-4-methyl-phenyl)-2,5-dimethyl-1H-imidazol-4-ylethynyl]-pyridine;
2-Chloro-4-[1-(3-fluoro-4-methoxy-phenyl)-2,5-dimethyl-1H-imidazol-4-ylethynyl]-pyridine;
2-Chloro-4-[1-(4-methoxy-phenyl)-2,5-dimethyl-1H-imidazol-4-ylethynyl]-pyridine;
2-Chloro-4-[2,5-dimethyl-1-(4-trifluoromethoxy-phenyl)-1H-imidazol-4-ylethynyl]-pyridine;
2-Chloro-4-[2,5-dimethyl-1-(3-trifluoromethoxy-phenyl)-1H-imidazol-4-ylethynyl]-pyridine; and
2-Chloro-4-[2,5-dimethyl-1-(4-trifluoromethyl-phenyl)-1H-imidazol-4-ylethynyl]-pyridine.

7. A process for preparing a compound of formula Ia which process comprises reacting a compound of formula II

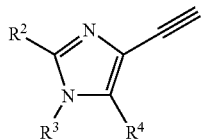
(II)

with a compound of formula III

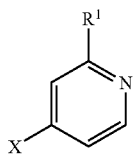
(III)

to obtain the compound of formula Ia;

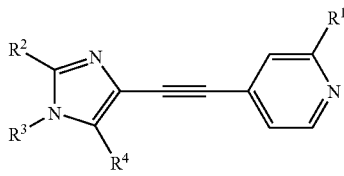
(Ia)

wherein
R$^1$ is halogen or cyano;
R$^2$ is lower alkyl;
R$^3$ is phenyl, pyridinyl, or a diazine optionally substituted by
one, two or three substituents selected from the group consisting of halogen, lower alkyl, lower alkoxy, cycloalkyl, lower haloalkyl, lower haloalkoxy, cyano, NR'R" or by
1-morpholinyl or by
1-pyrrolidinyl, optionally substituted by $(CH_2)_m$OR, or by
piperidinyl, optionally substituted by $(CH_2)_m$OR, or by
1,1-dioxo-thiomorpholinyl or by
piperazinyl, optionally substituted by lower alkyl or $(CH_2)_m$-cycloalkyl;
R is hydrogen, lower alkyl or $(CH_2)_m$-cycloalkyl;
R' and R" are each independently hydrogen, lower alkyl, $(CH_2)_m$-cycloalkyl or $(CH_2)_n$OR;
m is 0 or 1;
n is 1 or 2; and
R$^4$ is $CHF_2$, $CF_3$, C(O)H, or $CH_2R^5$ wherein R$^5$ is hydrogen, OH, $C_1$-$C_6$-alkyl or $C_3$-$C_{12}$-cycloalkyl;
X is halogen.

8. A process for preparing a compound of formula Ia which process comprises reacting a compound of formula IV

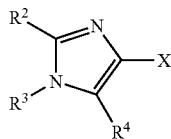
(IV)

with a compound of formula V

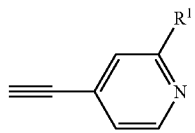
(V)

to obtain the compound of formula Ia;

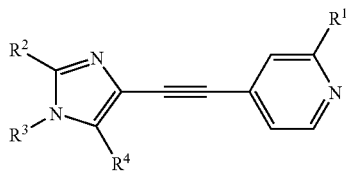
(Ia)

wherein
R$^1$ is halogen or cyano;
R$^2$ is lower alkyl;
R$^3$ is phenyl, pyridinyl, or a diazine optionally substituted by
one, two or three substituents selected from the group consisting of halogen, lower alkyl, lower alkoxy, cycloalkyl, lower haloalkyl, lower haloalkoxy, cyano, NR'R" or by
1-morpholinyl or by
1-pyrrolidinyl, optionally substituted by $(CH_2)_m$OR, or by
piperidinyl, optionally substituted by $(CH_2)_m$OR, or by
1,1-dioxo-thiomorpholinyl or by
piperazinyl, optionally substituted by lower alkyl or $(CH_2)_m$-cycloalkyl;
R is hydrogen, lower alkyl or $(CH_2)_m$-cycloalkyl;
R' and R" are each independently hydrogen, lower alkyl, $(CH_2)_m$-cycloalkyl or $(CH_2)_n$OR;
m is 0 or 1;
n is 1 or 2; and
R$^4$ is $CHF_2$, $CF_3$, C(O)H, or $CH_2R^5$ wherein R$^5$ is hydrogen, OH, $C_1$-$C_6$-alkyl or $C_3$-$C_{12}$-cycloalkyl.
X is halogen.

9. A process for preparing a compound of formula Ia which process comprises reacting a compound of formula Ic

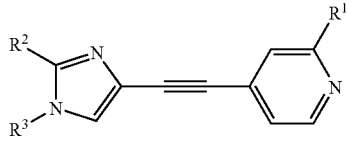
(Ic)

with a compound of formula VI

R$^4$—X
(VI)

to obtain the compound of formula Ia;

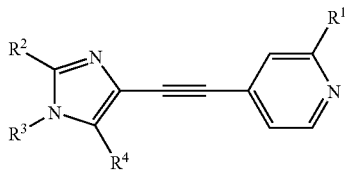

wherein
R¹ is halogen or cyano;
R² is lower alkyl;
R³ is phenyl, pyridinyl, or a diazine optionally substituted by
one, two or three substituents selected from the group consisting of halogen, lower alkyl, lower alkoxy, cycloalkyl, lower haloalkyl, lower haloalkoxy, cyano, NR'R" or by
1-morpholinyl or by
1-pyrrolidinyl, optionally substituted by $(CH_2)_m OR$, or by
piperidinyl, optionally substituted by $(CH_2)_m OR$, or by
1,1-dioxo-thiomorpholinyl or by
piperazinyl, optionally substituted by lower alkyl or $(CH_2)_m$-cycloalkyl;
R is hydrogen, lower alkyl or $(CH_2)_m$-cycloalkyl;
R' and R" are each independently hydrogen, lower alkyl, $(CH_2)_m$-cycloalkyl or $(CH_2)_n OR$;
m is 0 or 1;
n is 1 or 2; and
$R^4$ is $CHF_2$, $CF_3$, C(O)H, or $CH_2 R^5$ wherein $R^5$ is hydrogen, OH, $C_1$-$C_6$-alkyl or $C_3$-$C_{12}$-cycloalkyl;
X is halogen.

10. A pharmaceutical composition comprising a therapeutically effective amount of a compound of formula Ia

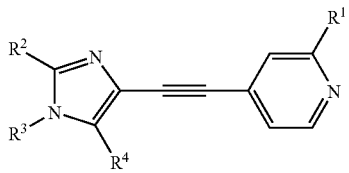

wherein
R¹ is halogen or cyano;
R² is lower alkyl;
R³ is phenyl, pyridinyl, or a diazine optionally substituted by
one, two or three substituents selected from the group consisting of halogen, lower alkyl, lower alkoxy, cycloalkyl, lower haloalkyl, lower haloalkoxy, cyano, NR'R" or by
1-morpholinyl or by
1-pyrrolidinyl, optionally substituted by $(CH_2)_m OR$, or by
piperidinyl, optionally substituted by $(CH_2)_m OR$, or by
1,1-dioxo-thiomorpholinyl or by
piperazinyl, optionally substituted by lower alkyl or $(CH_2)_m$-cycloalkyl;
R is hydrogen, lower alkyl or $(CH_2)_m$-cycloalkyl;
R' and R" are each independently hydrogen, lower alkyl, $(CH_2)_m$-cycloalkyl or $(CH_2)_n OR$;
m is 0 or 1;
n is 1 or 2; and
$R^4$ is $CHF_2$, $CF_3$, C(O)H, or $CH_2 R^5$ wherein $R^5$ is hydrogen, OH, $C_1$-$C_6$-alkyl or $C_3$-$C_{12}$-cycloalkyl;
or a pharmaceutically acceptable salt thereof and a pharmaceutically acceptable excipient.

11. A compound of formula Ia in accordance with claim 7 which is selected from the group consisting of
2-Chloro-4-[2,5-dimethyl-1-(3-methyl-4-trifluoromethoxy-phenyl)-1H-imidazol-4-ylethynyl]-pyridine;
2-Chloro-4-[1-(4-chloro-phenyl)-2,5-dimethyl-1H-imidazol-4-ylethynyl]-pyridine;
2-Chloro-4-[1-(3-chloro-2-fluoro-phenyl)-2,5-dimethyl-1H-imidazol-4-ylethynyl]-pyridine;
2-Chloro-4-[2,5-dimethyl-1-(3-trifluoromethyl-phenyl)-1H-imidazol-4-ylethynyl]-pyridine;
2-Chloro-4-[1-(3-chloro-4-fluoro-phenyl)-2,5-dimethyl-1H-imidazol-4-ylethynyl]-pyridine;
2-Chloro-4-[2,5-dimethyl-1-(2-methyl-4-trifluoromethoxy-phenyl)-1H-imidazol-4-ylethynyl]-pyridine;
2-Chloro-4-[5-difluoromethyl-1-(4-fluoro-phenyl)-2-methyl-1H-imidazol-4-ylethynyl]-pyridine;
[5-(2-Chloro-pyridin-4-ylethynyl)-3-(4-fluoro-phenyl)-2-methyl-3H-imidazol-4-yl]-methanol;
2-Chloro-4-[1-(4-methoxy-3-trifluoromethyl-phenyl)-2,5-dimethyl-1H-imidazol-4-ylethynyl]-pyridine;
2-Chloro-4-[1-(3,5-difluoro-4-methoxy-phenyl)-2,5-dimethyl-1H-imidazol-4-ylethynyl]-pyridine;
2-Chloro-4-[1-(4-methoxy-3-trifluoromethoxy-phenyl)-2,5-dimethyl-1H-imidazol-4-ylethynyl]-pyridine; and
2-Chloro-4-[1-(3-methoxy-4-trifluoromethoxy-phenyl)-2,5-dimethyl-1H-imidazol-4-ylethynyl]-pyridine.

12. A compound of formula Ia in accordance with claim 7 which is selected from the group consisting of
4-{3-[4-(2-Chloro-pyridin-4-ylethynyl)-2,5-dimethyl-imidazol-1-yl]-5-fluoro-phenyl}-morpholine;
2-Chloro-4-[1-(4-fluoro-2-trifluoromethoxy-phenyl)-2,5-dimethyl-1H-imidazol-4-ylethynyl]-pyridine;
2-Chloro-4-[1-(2-fluoro-4-trifluoromethoxy-phenyl)-2,5-dimethyl-1H-imidazol-4-ylethynyl]-pyridine;
2-Chloro-4-[2,5-dimethyl-1-(4-methyl-3-trifluoromethyl-phenyl)-1H-imidazol-4-ylethynyl]-pyridine;
2-Chloro-4-[2,5-dimethyl-1-(3-methyl-4-trifluoromethyl-phenyl)-1H-imidazol-4-ylethynyl]-pyridine;
2-Chloro-4-[2,5-dimethyl-1-(3-methyl-5-trifluoromethyl-phenyl)-1H-imidazol-4-ylethynyl]-pyridine;
2-Chloro-4-[1-(3-methoxy-5-trifluoromethyl-phenyl)-2,5-dimethyl-1H-imidazol-4-ylethynyl]-pyridine;
2-Chloro-4-[1-(3-methoxy-4-trifluoromethyl-phenyl)-2,5-dimethyl-1H-imidazol-4-ylethynyl]-pyridine;
2-Chloro-4-[1-(3,5-dichloro-phenyl)-2,5-dimethyl-1H-imidazol-4-ylethynyl]-pyridine;
2-Chloro-4-[1-(3-chloro-5-methyl-phenyl)-2,5-dimethyl-1H-imidazol-4-ylethynyl]-pyridine;
2-Chloro-4-[1-(3-fluoro-5-methyl-phenyl)-2,5-dimethyl-1H-imidazol-4-ylethynyl]-pyridine;
2-Chloro-4-[1-(3-chloro-5-methoxy-phenyl)-2,5-dimethyl-1H-imidazol-4-ylethynyl]-pyridine; and
2-Chloro-4-[1-(3-fluoro-5-methoxy-phenyl)-2,5-dimethyl-1H-imidazol-4-ylethynyl]-pyridine.

* * * * *